US007815908B2

(12) United States Patent
Sheppard et al.

(10) Patent No.: US 7,815,908 B2
(45) Date of Patent: Oct. 19, 2010

(54) METHODS AND COMPOSITIONS FOR TREATING AND PREVENTING DISEASE ASSOCIATED WITH αVβ5 INTEGRIN

(75) Inventors: Dean Sheppard, Oakland, CA (US); Amha Atakilit, Hayward, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 12/505,366

(22) Filed: Jul. 17, 2009

(65) Prior Publication Data
US 2009/0280118 A1 Nov. 12, 2009

Related U.S. Application Data

(62) Division of application No. 11/095,945, filed on Mar. 30, 2005, now abandoned.

(60) Provisional application No. 60/559,175, filed on Apr. 2, 2004.

(51) Int. Cl.
C07K 16/28 (2006.01)
A61K 39/395 (2006.01)

(52) U.S. Cl. .............. 424/143.1; 424/144.1; 424/133.1; 530/388.22

(58) Field of Classification Search ........................ None
See application file for complete search history.

(56) References Cited

U.S. PATENT DOCUMENTS

| | | | |
|---|---|---|---|
| 5,519,138 A | 5/1996 | Ries et al. | |
| 5,527,679 A | 6/1996 | Hemler et al. | |
| 5,780,426 A | 7/1998 | Palladino et al. | |
| 6,069,158 A | 5/2000 | Miller et al. | |
| 6,291,196 B1* | 9/2001 | Vielkind | 435/7.23 |
| 6,683,051 B1 | 1/2004 | Jonczyk et al. | |
| 6,692,741 B2 | 2/2004 | Huang et al. | |
| 7,053,041 B1* | 5/2006 | Brooks et al. | 514/2 |
| 2002/0037889 A1 | 3/2002 | Duggan et al. | |
| 2002/0072500 A1 | 6/2002 | Rogers et al. | |
| 2002/0077321 A1 | 6/2002 | Khanna et al. | |
| 2003/0139398 A1 | 7/2003 | Hoekstra et al. | |
| 2003/0171271 A1 | 9/2003 | Baciu et al. | |
| 2003/0181440 A1 | 9/2003 | Costanzo et al. | |
| 2004/0010023 A1 | 1/2004 | Stahle et al. | |
| 2004/0018192 A1 | 1/2004 | Wakabayashi et al. | |
| 2004/0019035 A1 | 1/2004 | Patane | |
| 2004/0019037 A1 | 1/2004 | Askew et al. | |
| 2004/0019206 A1 | 1/2004 | Ruminiski et al. | |

FOREIGN PATENT DOCUMENTS

| | | |
|---|---|---|
| DE | 4142366 | 6/1993 |
| WO | WO 98/14192 | 4/1998 |
| WO | WO 98/30542 | 7/1998 |
| WO | WO 99/07405 | 2/1999 |
| WO | WO 02/12501 | 2/2002 |
| WO | WO 2004/020435 | 3/2004 |

OTHER PUBLICATIONS

European Search Report dated Aug. 13, 2008, for related European Patent Application No. 05763460.2, filed Mar. 30, 2005.
Bransh, A.D., "A good antisense molecule is hard to find," Feb. 1998, Trends Biochem Sci., 23(2); 45-50.
Brooks et al. "Insulin-like Growth Factor Receptor Cooperates With Integrin αvβ5 to Promote Tumor Cell Dissemination In Vivo." *J. Clin. Invest.* (Mar. 1997), 99(6):1390-1398.
Chorev et al. "Approach to Discovering Novel Therapeutic Agents for Osteoporosis Based on Integrin Receptor Blockade." *Biopolymers* (1995), 37:367-375.
Elicieri et al. "Src-mediated coupling of focal adhesion kinase to integrin αvβ5 in vascular endothelial growth factor signaling." *J. Cell Biol.* (Apr. 2002), 157(1):149-159.
Friedlander et al. "Definition of Two Angiogenic Pathways by Distinct $α_v$ Integrins." *Science* (Dec. 1995), 270(5241):1500-1502.
Friedlander et al. "Involvement of integrins $α_vβ_3$ and $α_vβ_5$ in ocular neovascular diseases." *Proc. Natl. Acad. Sci. USA* (Sep. 1996), 93(18):9764-9769.
Goodman et al. "Nanomolar Small Molecule Inhibitors for αvβ6, αvβ5, and αvβ3 Integrins." *J. Med Chem.* (2002), 45(5):1045-1051.
Heba et al. "The Time Course of Tumor Necrosis Factor-α, Inducible Nitric Oxide Synthase and Vascular Endothelial Growth Factor Expression in an Experimental Model of Chronic Myocardial Infarction in Rats." *J. Vasc. Res.* (2001), 38(3):288-300.
Huang, Xiaozhu et al.; "Normal Development, Wound Healing, and Adenovirus Susceptibility in β5-Deficient Mice"; 2000, *Molecular and Cellular Biology*, vol. 20, No. 3, pp. 755-759.
Huang, Z., "Structural chemistry and therapeutic intervention of protei-protein interactions in immune response, human immunodeficiency virus entry, and apoptosis," Jun. 2000, Pharmacol Ther., 86(3), 2001-215.
Hynes, Richard O. "Integrins: Versatility, Modulation, and Signaling in Cell Adhesion." *Cell* (Apr. 1992), 69:11-25.
Kakouros et al. "Non-Cardiogenic Pulmonary Edema." *Hellenic J. Cardiol.* (2003), 44:385-391.
Li et al. "VEGF, *flk*-1, and *flt*-1 expression in a rat myocardial infarction model of angiogenesis." *Am. J. Physiol.* (1996), 270(5 Pt 2):H1803-H1811.
Mountain, A., "Gene therapy: the first decade." Mar. 2000, Trends Biotechnol., 18(3): 119-128.
Pasqualini et al. "A Peptide Isolated from Phage Display Libraries Is a Structural and Functional Mimic of an RGD-binding Site on Integrins." *J. Cell. Biol.* (Sep. 1995), 130(5):1189-1196.
Pasqualini et al. "A study of the structure, function and distribution of β5 integrins using novel anti-β5 monoclonal antibodies." *J. Cell Science* (1993), 105:101-111.
Pasqualini et al. "Contrasting Roles for Integrin $β_1$ and $β_5$ Cytoplasmic Domains in Subcellular Localization, Cell Proliferation, and Cell Migration." *J. Cell Biology* (Apr. 1994), 125(2):447-460.

(Continued)

*Primary Examiner*—Maher M Haddad
(74) *Attorney, Agent, or Firm*—Townsend and Townsend and Crew, LLP

(57) ABSTRACT

The present invention provides compositions and methods for treating and preventing disease associated with αvβ5 integrin by blocking binding to αvβ5 integrin.

9 Claims, 4 Drawing Sheets

OTHER PUBLICATIONS

Pasqualini, R., Bodorova, J., Ye, S. and Hemler, M.E., "A study of the structure, function and distribution of beta 5 integrins using novel anti-beta5 monoclonal antibodies," 1993, J. Cell Sci., 105, 101-111.

Pierschbacher et al. "Manipulation of Cellular Interactions With Biomaterials Toward a Therapeutic Outcome: A Perspective." *J. Cell Biochem.* (1994), 56:150-154.

Ruoslahti, E. "RGD And Other Recognition Sequences For Integrins." *Ann. Rev. Cell. Dev. Biol.* (1996), 12:697-715.

Smith et al. "Building Synthetic Antibodies as Adhesive Ligands for Integrins." *J. Biol. Chem.* (Dec. 1994), 269(52):32788-32795.

Soeki et al. "Serial Changes in Serum VEGF and HGF in Patients with Acute Myocardial Infarction." *Cardiology* (2000), 93(3):168-174.

Toole et al., Storming Media: the role of EMMPRIN in Tumor angiogenesis and metastasis, abstract, May 2001.

Wang et al., "A single amino acid determines lysophospholipid specificity of the S1P1 (EDG1) and LPA1 (EDG2) phospholipid growth factor receptors," Dec. 2001, J. Biol. Chem. 276(52): 49213-49220.

Wayner et al. "Integrins αvβ3 and αvβ5 Contribute to Cell Attachment to Vitronectin but Differentially Distribute on the Cell Surface." *J. Cell Biol.* (May 1991), 113(4):919-929.

* cited by examiner

METHODS AND COMPOSITIONS FOR TREATING AND PREVENTING DISEASE ASSOCIATED WITH αVβ5 INTEGRIN

CROSS REFERENCE TO RELATED APPLICATIONS

This application is a divisional application of U.S. patent application Ser. No. 11/095,945, filed Mar. 30, 2005, which claims the benefit of U.S. Provisional Patent Application No. 60/559,175, filed Apr. 2, 2004, each of which is incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. HL53949, awarded by the National Institutes of Health. The government has certain rights in this invention.

BACKGROUND OF THE INVENTION

Pulmonary edema ("PE") affects millions of people each year, causing substantial morbidity and mortality. In PE patients, the alveoli flood with liquid from pulmonary capillaries which compromises oxygen transfer to the systemic circulation (Hall, et al. in CURRENT THERAPY IN RESPIRATORY MEDICINE (R. Cherniack, Ed., 1986), pp. 222-227). This sequence of events results in hypoxemia, hypercapnia, and death if no corrective measures are taken.

Any condition or agent that disrupts fluid homeostasis in the lungs can result in PE, which can be broadly divided into cardiogenic and non-cardiogenic PE (see, e.g., Kakouros and Kakouros, *Hellenic J. Cardiol.* 44:385-391 (2003). For example, Acute Lung Injury/Adult (acute) Respiratory Distress Syndrome or "ARDS," which can develop as a result of lung injury due to, e.g., pneumonia, septic shock, trauma, aspiration of vomit, or chemical inhalation, is often associated with non-cardiogenic PE. Non-cardiogenic PE is characterized by a change in the vascular permeability of the lung tissue which leads to an increase in fluid levels in the lungs. Cardiogenic PE is often caused by left sided heart failure and can be a complication of a heart attack, leaking or narrowed heart valves (mitral or aortic valves), or any disease of the heart that either results in weakening and/or stiffening of the heart muscle (cardiomyopathy). The failing heart transmits its increased pressure to the lung veins. As pressure in the lung veins rises, fluid is pushed into the air spaces (alveoli). This fluid then becomes a barrier to normal oxygen exchange, resulting in shortness of breath. Cardiogenic PE is characterized by increased capillary hydrostatic pressure which leads to an increase in fluid levels in the lungs.

PE is caused by, e.g., altered capillary permeability; infection; inhaled or circulating toxins; vasoactive substances (e.g., histamine, kinins); disseminated intravascular coagulation; immunologic reactions; radiation-associated pneumonia; uremia; near-drowning; smoke inhalation; and acute respiratory distress syndrome; left ventricular failure; mitral stenosis; bacterial endocarditis; pulmonary venous fibrosis; congenital stenosis of the origin of the pulmonary veins; pulmonary venoocclusive disease; overinfusion of fluids; hypoalbuminemia (e.g., from renal, hepatic, nutritional, or protein-losing enteropathy); high-altitude; drug overdoses, CNS trauma, subarachnoid bleeding, pulmonary embolism, pulmonary parenchymal disease, eclampsia, anesthesia, and cardiopulmonary bypass operations.

Symptoms of PE may include, for example, shortness of breath, rapid and/or labored breathing, tachycardia, hypertension, tightness in the chest, cold extremities with or without accompanying cyanosis, cough with a frothy or pink sputum, extensive use of accessory muscles of respiration, moist rales with or without wheezing, and combinations thereof. Tests to diagnose PE include blood tests such as complete blood count (CBC), blood urea nitrogen (BUN), creatinine, and serum protein. Urianalysis, arterial blood gases (ABGs), chest X-rays, and electrocardiograms (ECG) and all used to assist the physician in narrowing the diagnosis down to PE.

Treatment of cardiogenic PE typically involves placing the patient on 100% oxygen, morphine to ease anxiety and provide some beneficial cardiac effects, furosemide for diuresis, vasodilators to reduce the work against which the myocardium must pump, and inotropic drugs such as doputamine to increase cardiac contractility. Other measures that have been used are rotating tourniquets on three of four limbs and reducing blood volume by 500 ml.

Unfortunately, no specific or satisfactorily effective treatment for PE is available. Thus, there is a need in the art for more effective and specific therapies for PE. The present invention addresses this and other problems.

BRIEF SUMMARY OF THE INVENTION

The present invention provides compositions and methods for treating or preventing diseases involving αvβ5 integrin such as PE.

One embodiment of the present invention provides methods of treating or preventing PE in a mammalian subject (e.g., a primate such as a human, a monkey, or a chimpanzee; a canine; or a feline). A therapeutic amount or prophylactic amount of an antagonist of αvβ5 integrin is administered to the subject. The antagonist may be, for example, an agent under 1 kDa, under 0.5 KDa, or under 0.25 KDa. The antagonist may be an antibody or an antibody fragment, including humanized antibodies, scFv, Fab, or (Fab')2. The antibody may be ALULA, humanized ALULA, or may compete with ALULA for specific binding to αvβ5 integrin. Administration may be, but is not limited to intravenous, intra-nasal, or intra-bronchial. The methods of the invention are useful for treating individuals that have PE or are at risk of developing PE. A second therapeutic agent for treating or preventing acute lung injury and/or ARDS and or PE may be administered to the subject, including, but not limited to, e.g., TGFβ pathway inhibitors, activated Protein C, steroids, GM-CSF, diuretic agents, bronchodilating agents, platelet inhibitors, an antibody that binds to αvβ5 integrin, an antibody that binds to β5, a second antagonist of αvβ5 integrin, an antagonist of αvβ6 integrin, a β2 agonist, or a surfactant.

Another embodiment of the invention provides an antibody that specifically competes with ALULA for binding to αvβ5 integrin. The antibody of this embodiment may be ALULA itself, humanized ALULA, a fragment of ALULA including, e.g., a scFv, a Fab, and a (Fab')2 of ALULA, or another antibody that competes with ALULA for binding to αvβ5 integrin. The invention also provides pharmaceutical compositions comprising such antibodies and a pharmaceutically acceptable excipient. The pharmaceutical compositions may further comprise a second therapeutic agent (e.g., a TGFβ pathway inhibitor, activated Protein C, a steroid, GM-CSF, a platelet inhibitor, a diuretic agent; a bronchodilating agent, an antibody that binds to αvβ5 integrin, an antibody that binds to β5, a second antagonist of αvβ5 integrin, and an antagonist of αvβ6 integrin) that treats or prevents PE. Alternately, the pharmaceutical compositions may comprise a therapeutic agent for stroke, myocardial infarction, and cancer (i.e., angiogenesis).

A further embodiment of the invention provides methods of identifying an agent for treating PE. In some embodiments, the methods comprise contacting a plurality of agents with αvβ5 integrin, selecting an agent that competes with binding of a ligand to αvβ5 integrin, and determining the effect of the selected agent on PE. Agents which have an effect on PE are identified as agents for treating PE. The plurality of agents may be a plurality of antibodies or may be under 1 KDa. The ligand may be an antibody, including, e.g., ALULA, or may be vitronectin, fibronectin, osteopontin, tenascin c and adenovirus penton base.

Another embodiment of the invention provides kits for treating or preventing PE. The kits comprise an antagonist of αvβ5 integrin (e.g., a monoclonal antibody including ALULA, and antibodies that compete with ALULA for binding to αvβ5 integrin) and a second therapeutic agent for treating pulmonary edema (e.g., a TGFβ pathway inhibitor, activated Protein C, a steroid, GM-CSF, a platelet inhibitor, a diuretic agent; a bronchodilating agent, an antibody that binds to αvβ5 integrin, an antibody that binds to β5, a second antagonist of αvβ5 integrin, an antagonist of αvβ6 integrin, a β2 agonist, or a surfactant.

These and other embodiments of the invention are further illustrated by the detailed description that follows.

DETAILED DESCRIPTION OF THE INVENTION

I. Introduction

Figure 1:
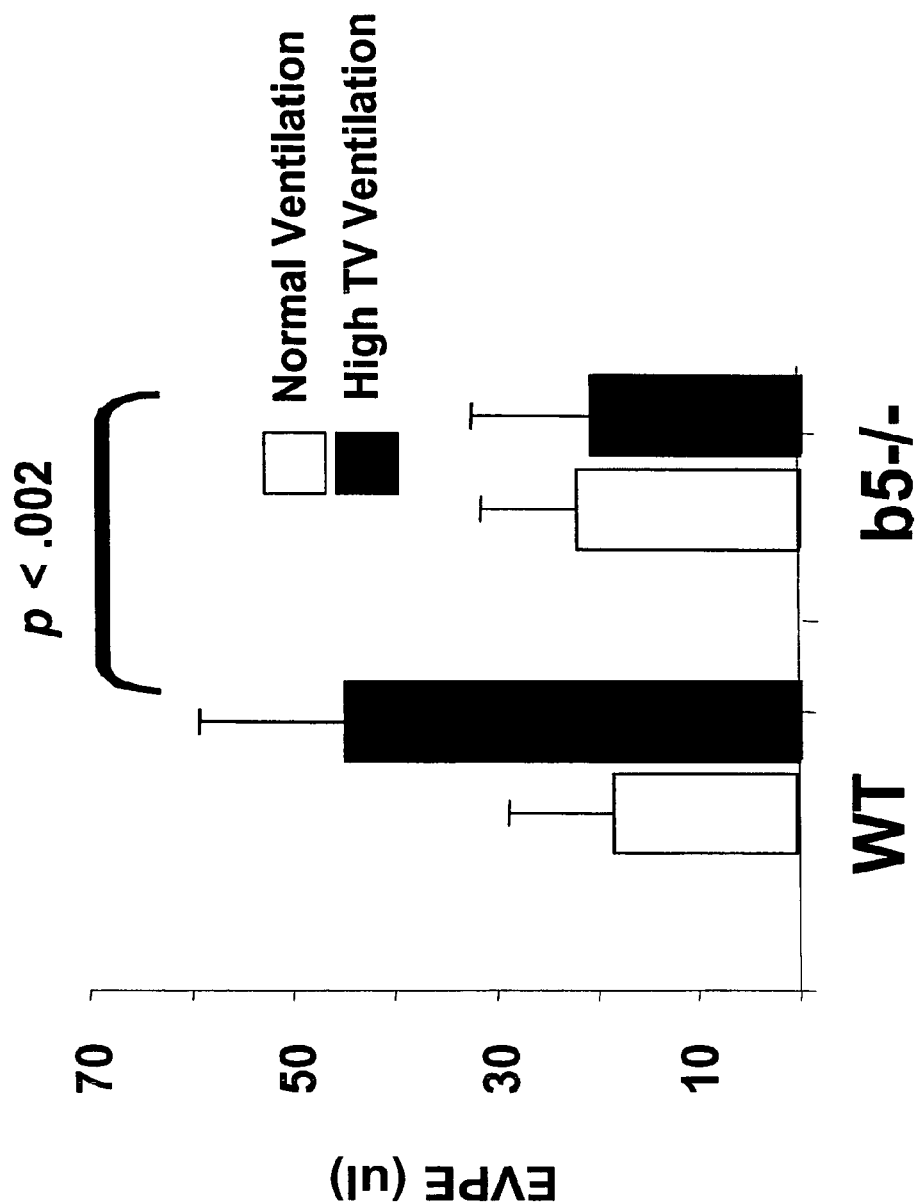
FIG. 1 illustrates results from in vivo experiments that demonstrate that β5$^{-/-}$ mice are protected from lung injury induced PE.

The present invention is based in part on the surprising discovery that treating animals with agents that bind to αvβ5 integrins reduces symptoms of PE. More particularly, blocking binding of ligands to αvβ5 integrin can reduce the severity of PE. The inventors have demonstrated that an antibody that binds to αvβ5 integrin blocks binding of vitronectin, a ligand of αvβ5 integrin, to αvβ5 integrin. The inventors have further demonstrated that administration of an antibody that binds to αvβ5 integrin reduces the severity of PE. Accordingly, the invention provides methods of treating or preventing PE in a subject by administering an effective amount of an antagonist of αvβ5 to the subject.

The invention also provides antibodies that compete with the disclosed antibody designated "ALULA" as well as pharmaceutical compositions comprising such antibodies. As described in greater detail in the Examples below, ALULA binds to αvβ5 integrin and administration of ALULA to a mammalian subject reduces the severity of PE in the subject.

The invention also provides methods of identifying new agents for the treatment of PE by identifying agents that interact with αvβ5 integrins and testing them for their ability to treat PE.

II. Definitions

An "αvβ5 antagonist" is any agent that competes with an αvβ5 ligand for available ligand binding sites on αvβ5 integrins. αvβ5 antagonists include agents that specifically bind to αvβ5, β5, as well as agent that bind to αvβ5 or β5 and at least one other integrin such as, e.g., αvβ3 or αvβ6.

An αvβ5 integrin is a member of a family of adhesion molecules that comprise non-covalently associated α/β heterodimers that mediate, inter alia, cell-cell interactions, cell-extracellular matrix interactions, and cell-pathogen interactions. αvβ5 is the only integrin that contains the β5 subunit. αvβ5 recognizes the RGD peptide sequence and binds vitronectin (see, e.g., Hynes, *Cell* 69:11-25 (1992) and has been implicated in multiple disorders including stroke, myocardial infarction, cancer (i.e., angiogenesis), and ocular neovascularization disease (see, e.g., Friedlander et al., *Science* 270 (5241):1500-2 (1995); Friedlander et al, *PNAS USA* 93 (18): 9764-9 (1996); Elicieri et al., *J. Cell Biol.* 157 (10:149-159 (2002); Heba et al., *J. Vasc. Res.* 38 (3):288-300 (2001); Soeki et al., *Cardiology* 93 (3):168-74 (2000); and Li et al, *Am. J. Physiol.* 270 (5 Pt 2):H1803-11 (1996). αv and β5 have both been sequenced and characterized (see, e.g., Hynes, 1992 supra, and U.S. Pat. No. 5,527,679, respectively).

A "therapeutic dose" or "therapeutically effective amount" or "effective amount" of an αvβ5 integrin antagonist is an amount of the antagonist which prevents, alleviates, abates, or reduces the severity of symptoms of diseases associated with αvβ5 integrin including, e.g., stroke, myocardial infarction, cancer (i.e., angiogenesis), ocular neovascularization disease, and PE (e.g., fluid accumulation in the lungs, increased pulmonary capillary hydrostatic pressure, or shortness of breath) in a patient.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. Thus, the terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993), *PNAS. USA* 90:6444, Gruber et al. (1994) *J Immunol.* :5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *PNAS USA*, 81:6851-6855 (1984); Morrison and Oi, *Adv. Immunol.*, 44:65-92 (1988); Verhoeyen et al., *Science,* 239:1534-1536 (1988); Padlan, *Molec. Immuno.*, 28:489-498 (1991); Padlan, *Molec. Immun.*, 31 (3):169-217 (1994).

"Single chain Fv (scFv)" or "single chain antibodies" refers to a protein wherein the $V_H$ and the $V_L$ regions of a scFv antibody comprise a single chain which is folded to create an antigen binding site similar to that found in two chain antibodies. Methods of making scFv antibodies have been described in e.g., Ward et al., *Exp Hematol.* (5):660-4 (1993); and Vaughan et al, *Nat. Biotechnol.* 14 (3):309-14 (1996). Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser, e.g., 2, 3, 4, 5, or 6 such sequences. However, it is to be appreciated that some amino acid substitutions within the linker can be made. For example, a valine can be substituted for a glycine. Additional peptide linkers and their use are well-known in the art. See, e.g., Huston et al., *Proc. Nat'l Acad. Sci. USA* 8:5879 (1988); Bird et al, *Science* 242:4236 (1988); Glockshuber et al., *Biochemistry* 29:1362 (1990); U.S. Pat. No. 4,946,778, U.S. Pat. No. 5,132,405 and Stemmer et al., *Biotechniques* 14:256-265 (1993).

The phrase "specifically (or selectively) binds to an antibody" when referring to a protein or peptide, refers to a binding reaction which is determinative of the presence of the protein in the presence of a heterogeneous population of proteins and other biologics. Thus, under designated immunoassay conditions, the specified antibodies bind to a particular protein (e.g., αvβ5 integrin, β5, or portions thereof) and do not bind in a significant amount to other proteins present in the sample. Specific binding to an antibody under such conditions may require an antibody that is selected for its specificity for a particular protein. For example, antibodies raised against an αvβ5 integrins or a β5 polypeptide can be selected to obtain antibodies specifically immunoreactive with that protein and not with other proteins, except for polymorphic variants, e.g., proteins at least 80%, 85%, 90%, 95% or 99% identical to a sequence of interest. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

An agent that "specifically competes" for binding reduces the specific binding of an antibody to a polypeptide. A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the competitive binding assays known in the art (see, e.g., Harlow and Lane, supra).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "peptidomimetic" and "mimetic" refer to a synthetic chemical compound that has substantially the same structural and functional characteristics of the αvβ5 antagonists of the invention. Peptide analogs are commonly used in the pharmaceutical industry as non-peptide drugs with properties analogous to those of the template peptide. These types of non-peptide compound are termed "peptide mimetics" or "peptidomimetics" (see, e.g., Fauchere, *J. Adv. Drug Res.* 15:29 (1986); Veber and Freidinger *TINS* p. 392 (1985); and Evans et al. *J. Med. Chem.* 30:1229 (1987)). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a naturally occurring αvβ5 ligand, but have one or more peptide linkages optionally replaced by a linkage selected from the group consisting of, e.g., —CH2NH—, —CH2S—, —CH2-CH2-, —CH═CH— (cis and trans), —COCH2-, —CH(OH)CH2-, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As used herein, the terms "nucleic acid" and "polynucleotide" are used interchangeably. Use of the term "polynucleotide" includes oligonucleotides (i.e., short polynucleotides). This term also refers to deoxyribonucleotides, ribonucleotides, and naturally occurring variants, and can also refer to synthetic and/or non-naturally occurring nucleic acids (i.e., comprising nucleic acid analogues or modified backbone residues or linkages), such as, for example and without limitation, phosphorothioates, phosphoramidates, methyl phosphonates, chiral-methyl phosphonates, 2-O-methyl ribonucleotides, peptide-nucleic acids (PNAs), and the like. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (see, e.g., Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene (see, e.g., Bass, *Nature,* 411, 428-429 (2001); Elbashir et al., *Nature,* 411, 494-498 (2001); WO 00/44895; WO 01/36646; WO 99/32619; WO 00/01846; WO 01/29058; WO 99/07409; and WO 00/44914). "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferably about preferably about 20-30 base nucleotides, preferably about 20-25 nucleotides in length, e.g., 20, 21, 22, 23, 24, 25, 26, 27, 28, 29, or 30 nucleotides in length.

"Silencing" or "downregulation" refers to a detectable decrease of transcription and/or translation of a target sequence, i.e., the sequence targeted by the RNAi, or a decrease in the amount or activity of the target sequence or protein in comparison to the normal level that is detected in the absence of the interfering RNA or other nucleic acid sequence. A detectable decrease can be as small as 5% or 10%, or as great as 80%, 90% or 100%. More typically, a detectable decrease ranges from 20%, 30%, 40%, 50%, 60%, or 70%.

III. Inhibition of αvβ5

The present invention provides methods for treating or preventing diseases involving αvβ5 integrin such as, e.g., PE, stroke, myocardial infarction, cancer (e.g., by preventing αvβ5 integrin-associated angiogenesis), and ocular neovascular diseases (e.g., by preventing αvβ5 integrin-associated angiogenesis), by inhibiting binding of ligands to αvβ5 integrin. Any method that inhibits αvβ5 integrin expression or ligand binding to αvβ5 integrin can be used to treat diseases involving αvβ5 integrin according to the methods of the invention. For example, antibodies that specifically bind to αvβ5 integrin, antibodies that specifically bind to the β5 subunit, ligands of αvβ5 integrin, and peptide, non-peptide, and peptidomimetic analogs of such ligands can be used to inhibit binding to αvβ5 integrin and thus, treat or prevent diseases involving αvβ5. In addition, polynucleotides that inhibit expression of β5 (e.g., siRNA molecules, antisense sequences, etc.) can be used to treat or prevent diseases involving αvβ5 integrin. In some embodiments, the disease is PE (including, e.g., cardiogenic and non-cardiogenic PE). In some embodiments, treatment of PE also treats or prevents downstream disorders such as, e.g., pulmonary fibrosis.

A. Antibodies

According to one aspect of the present invention, antibodies that specifically bind to αvβ5 integrin or to the β5 subunit of the αvβ5 integrin, are used to treat or prevent diseases involving αvβ5 including, e.g., PE, stroke, myocardial infarction, cancer (i.e., angiogenesis), and ocular neovascular diseases (i.e., angiogenesis). The antibodies may also compete with other ligands for binding to αvβ5 integrin or to the β5 subunit of the αvβ5 integrin. Suitable antibodies include, e.g., monoclonal antibodies, humanized antibodies and antibody fragments (i.e., Fv, Fab, (Fab')$_2$, or scFv).

In some embodiments, the monoclonal antibody ALULA (ATCC Deposit No. PTA-5817, made Feb. 13, 2004, at the ATCC, 10801 University Blvd. Manassas, Va. 20110-2209) which binds to the β5 subunit of the αvβ5 integrin, is used to treat or prevent diseases involving αvβ5 integrin, including, e.g., PE, stroke, myocardial infarction, cancer (i.e., angiogenesis), and ocular neovascular diseases (i.e., angiogenesis). Without being bound by theory, it is postulated that ALULA acts by blocking αvβ5 integrin-mediated changes to vascular permeability in the lungs. In some embodiments, humanized ALULA, ALULA fragments, or a monoclonal antibody which competes with ALULA for binding to αvβ5 integrin or the β5 subunit of the αvβ5 integrin is used to treat PE.

Monoclonal antibodies are obtained by various techniques familiar to those skilled in the art. Briefly, spleen cells from an animal immunized with a desired antigen are immortalized, commonly by fusion with a myeloma cell (see, for example, Kohler & Milstein, *Eur. J. Immunol.* 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246: 1275-1281 (1989).

Monoclonal antibodies are collected and titered against the immunogen in an immunoassay, for example, a solid phase immunoassay with the immunogen immobilized on a solid support. Monoclonal antibodies will usually bind with a $K_d$ of at least about 0.1 mM, more usually at least about 1 µM, preferably at least about 0.1 µM or better, and most preferably, 0.01 µM or better.

In an exemplary embodiment, an animal, such as a rabbit or mouse is immunized with αvβ5 polypeptide, or an nucleic acid construct encoding such a polypeptide. The antibodies produced as a result of the immunization can be isolated using standard methods.

The immunoglobulins, including binding fragments and other derivatives thereof, of the present invention may be produced readily by a variety of recombinant DNA techniques, including by expression in transfected cells (e.g., immortalized eukaryotic cells, such as myeloma or hybridoma cells) or in mice, rats, rabbits, or other vertebrate capable of producing antibodies by well known methods. Suitable source cells for the DNA sequences and host cells for immunoglobulin expression and secretion can be obtained from a number of sources, such as the American Type Culture Collection (Catalogue of Cell Lines and Hybridomas, Fifth edition (1985) Rockville, Md.

In some embodiments, the antibody is a humanized antibody, i.e., an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., *PNAS USA*, 81:6851-6855 (1984); Morrison and Oi, *Adv. Immunol.*, 44:65-92 (1988); Verhoeyen et al., *Science*, 239:1534-1536 (1988); Padlan, *Molec. Immun.*, 28:489-498 (1991); Padlan, *Molec. Immun.*, 31 (3):169-217 (1994). Techniques for humanizing antibodies are well known in the art and are described in e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) *Nature* 321: 522; and Verhoyen et al. (1988) *Science* 239:1534. Humanized antibodies are further described in, e.g., Winter and Milstein (1991) *Nature* 349:293. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells. The CDRs for producing the immunoglobulins of the present invention will be similarly derived from monoclonal antibodies capable of specifically binding to αvβ5 integrin (e.g., ALULA or antibodies that compete with ALULA for specific binding to αvβ5 integrin).

In some cases, transfer of a CDR to a human framework leads to a loss of specificity for the humanized antibody. In these cases, back mutation can be introduced into the framework regions of the human portion of the antibody. Methods of making back mutations are well known in the art and are described in, e.g., Co et al, *PNAS USA* 88; 2269-2273 (1991) and WO 90/07861.

In some embodiments, the antibodies are antibody fragments such as Fab, F(ab')$_2$, Fv or scFv. The antibody fragments can be generated using any means known in the art including, chemical digestion (e.g., papain or pepsin) and recombinant methods. Methods for isolating and preparing recombinant nucleic acids are known to those skilled in the art (see, Sambrook et al., *Molecular Cloning. A Laboratory Manual* (2d ed. 1989); Ausubel et al., *Current Protocols in Molecular Biology* (1995)). The antibodies can be expressed in a variety of host cells, including *E. coli*, other bacterial hosts, yeast, and various higher eukaryotic cells such as the COS, CHO, and HeLa cells lines and myeloma cell lines.

One embodiment of the invention provides methods for identifying antibodies that compete with ALULA for specific binding to αvβ5 integrin.

Competitive binding assays can be used to identify antibodies that compete with ALULA for specific binding to αvβ5 integrin. Any of a number of competitive binding assays known in the art can be used to measure competition between two antibodies to the same antigen. Briefly, the ability of different antibodies to inhibit the binding of another antibody is tested. For example, antibodies can be differentiated by the epitope to which they bind using a sandwich ELISA assay. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

B. αvβ5 Small Molecule Antagonists

Any small molecule antagonist of αvβ5 can be used according to the methods of the invention to treat or prevent PE. Generally, the small molecules will be less than 1000 daltons in mass and will often be less than 500 daltons.

Exemplary αvβ5 small molecule antagonists include, e.g., those described in US Published Patent Application Nos. 2000/40019206, 2004/0019037, 2004/0019035, 2004/0018192, 2004/0010023, 2003/0181440, 2003/0171271, 2003/0139398, 2002/0037889, 2002/0077321, 2002/0072500, U.S. Pat. No. 6,683,051 and Goodman et al., *J. Med Chem.* 45 (5):1045-51 (2002).

For example, compounds of Formula I as set forth in U.S. Patent Publication No. 20040019206 A1 including their various isomers, enantiomers, tautomers, racemates and polymorphs can be used:

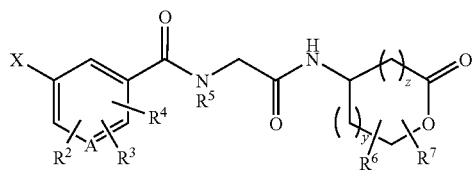

or a pharmaceutically acceptable salts thereof wherein
X is

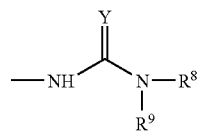

Y is selected from the group consisting of N—$R^1$, O, and S; y and z are independently selected from an integer selected from 0, 1, 2 and 3; A is N or C; $R^1$ is selected from the group consisting of H, alkyl, aryl, hydroxy, alkoxy, cyano, nitro, amino, alkenyl, alkynyl, amido, alkylcarbonyl, arylcarbonyl, alkoxycarbonyl, aryloxycarbonyl, haloalkylcarbonyl, haloalkoxycarbonyl, alkylthiocarbonyl, arylthiocarbonyl, acyloxymethoxycarbonyl, alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles, aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle, monocyclic heterocycles, and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^1$ taken together with $R^8$ forms a 4-12 membered dinitrogen containing heterocycle optionally substituted with one or more substituent selected from the group consisting of lower alkyl, hydroxy, keto, alkoxy, halo, phenyl, amino, carboxyl or carboxyl ester, and fused phenyl; or $R^1$ taken together with $R^8$ forms a 5 membered heteroaromatic ring optionally substituted with one or more substituent selected from lower alkyl, phenyl and hydroxy; or $R^1$ taken together with $R^8$ forms a 5 membered heteroaromatic ring fused with a phenyl group;

$R^8$ (when not taken together with $R^1$) and $R^9$ are independently selected from the group consisting of H, alkyl, alkenyl, alkynyl, aralkyl, amino, alkylamino, hydroxy, alkoxy, arylamino, amido, alkylcarbonyl, arylcarbonyl, alkoxycarbonyl, aryloxy, aryloxycarbonyl, haloalkylcarbonyl, haloalkoxycarbonyl, alkylthiocarbonyl, arylthiocarbonyl, acyloxymethoxycarbonyl, cycloalkyl, bicycloalkyl, aryl, acyl, benzoyl, alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles, monocyclic heterocycles, monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl, monocyclic and bicyclic heterocyclicalkyls, —$SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

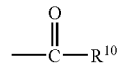

wherein
$R^{10}$ is defined as above; or
$NR^8$ and $R^9$ taken together form a 4-12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;
or
X is

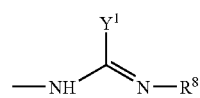

X is

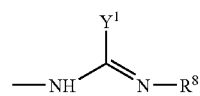

wherein
Y' is selected from the group consisting of alkyl, cycloalkyl, bicycloalkyl, aryl, monocyclic heterocycles, alkyl optionally substituted with aryl which can also be optionally substituted with one or more substituent selected from halo, haloalkyl, alkyl, nitro, hydroxy, alkoxy, aryloxy, aryl, or fused aryl, aryl optionally substituted with one or more substituent selected from halo, haloalkyl, hydroxy, alkoxy, aryloxy, aryl, fused aryl, nitro, methylenedioxy, ethylenedioxy, or alkyl, alkynyl, alkenyl, —S—$R^{11}$ and —O$R^{11}$ wherein $R^{11}$ is selected from the group consisting of H, alkyl, aralkyl, aryl, alkenyl, and alkynyl, or $R^{11}$ taken together with $R^8$ forms a 4-12 membered mononitrogen and monosulfur or monooxygen containing heterocyclic ring optionally substituted with lower alkyl, hydroxy, keto, phenyl, carboxyl or carboxyl ester, and fused phenyl, or $R^{11}$ taken together with $R^8$ is thiazole, oxazole, benzoxazole, or benzothiazole; $R^8$ is defined as above; or $Y^1$ (when $Y^1$ is carbon) taken together with $R^8$ forms a 4-12 membered mononitrogen or dinitrogen containing ring optionally substituted with alkyl, aryl, keto or hydroxy; or X is

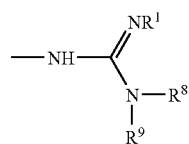

wherein $R^1$ and $R^8$ taken together form a 5-8 membered dinitrogen containing heterocycle optionally substituted with one or more substituent selected from the group consisting of lower alkyl, hydroxy, keto, phenyl, or carboxyl derivatives; and $R^9$ is selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl, or acyloxymethoxycarbonyl; or X is

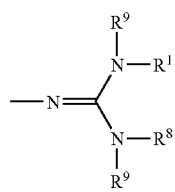

wherein $R^1$ and $R^8$ taken together form a 5-8 membered dinitrogen containing heterocycle optionally substituted with hydroxy, keto, phenyl, or alkyl; and $R^9$ are both selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl and acyloxymethoxycarbonyl;

$R^2$, $R^3$ and $R^4$ are independently selected from one or more substituent selected from the group consisting of H, alkyl, hydroxy, alkoxy, aryloxy, halogen, haloalkyl, haloalkoxy, nitro, amino, alkylamino, acylamino, dialkylamino, cyano, alkylthio, alkylsulfonyl, carboxyl derivatives, trihaloacetamide, acetamide, aryl, fused aryl, cycloalkyl, thio, monocyclic heterocycles, fused monocyclic heterocycles, and X, wherein X is defined as above;

$R^5$, $R^6$ and $R^7$ are independently selected from the group consisting of hydrogen, alkyl, alkenyl, alkynyl, aryl, carboxyl derivatives, haloalkyl, cycloalkyl, monocyclic heterocycles, monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido, alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, monocyclic heterocycles, and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl, alkylcarbonyl, haloalkylcarbonyl, and arylcarbonyl, aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, acyloxy, carboxyl derivatives, carboxyalkoxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles.

Compounds of Formula II as set forth in U.S. Patent Publication No. 20040019037 A1 including their various isomers, enantiomers, tautomers, racemates and polymorphs can also be used:

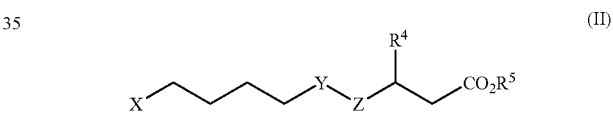

or a pharmaceutically acceptable salt thereof, wherein
X is selected from the group consisting of:

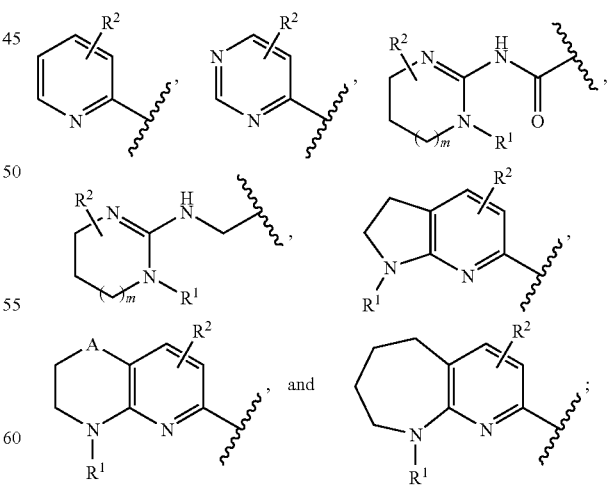

Y—Z is —$CH_2CH_2$— or —$CONR^3$—; A is O or $NR^1$; m is O or 1; $R^1$ is hydrogen or $C_{1-3}$ alkyl; each non-aromatic ring carbon atom is unsubstituted or independently substituted with one or two $R^2$ substituents and each aromatic ring carbon atom is unsubstituted or independently substituted with one $R^2$ substituent selected from the group consisting of: $C_{1-8}$ alkyl, $C_{3-8}$ cycloalkyl, $C_{3-8}$ cycloheteroalkyl, $C_{3-8}$ cycloalkyl-$C_{1-6}$ alkyl, $C_{3-8}$ cycloheteroalkyl-$C_{1-6}$ alkyl, aryl, aryl-$C_{1-6}$ alkyl, amino, amino-$C_{1-6}$ alkyl, $C_{1-3}$ acylamino, $C_{1-3}$ acylamino-$C_{1-6}$ alkyl, $(C_{1-6}$ alkyl$)_{1-2}$ amino, $C_{3-6}$ cycloalkyl-$C_{0-2}$ amino, $(C_{1-6}$ alkyl$)_{1-2}$ amino-$C_{1-6}$ alkyl, $C_{1-6}$ alkoxy, $C_{1-4}$ alkoxy-$C_{1-6}$ alkyl, hydroxycarbonyl, hydroxycarbonyl-$C_{1-6}$ alkyl, $C_{1-3}$ alkoxycarbonyl, $C_{1-3}$ alkoxycarbonyl-$C_{1-6}$ alkyl, hydroxy, hydroxy-$C_{1-6}$ alkyl, nitro, cyano, trifluoromethyl, trifluoromethoxy, trifluoroethoxy, $C_{1-8}$ alkyl-$S(O)_{0-2}$, $(C_{1-8}$ alkyl$)_{0-2}$ aminocarbonyl, $C_{1-8}$ alkyloxycarbonylamino, $(C_{1-8}$ alkyl$)_{1-2}$ aminocarbonyloxy, (aryl $C_{1-3}$ alkyl$)_{1-2}$ amino, (aryl$)_{1-2}$ amino, aryl-$C_{1-3}$ alkylsulfonylamino, and $C_{1-8}$ alkylsulfonylamino; or two $R^2$ substituents, when on the same non-aromatic carbon atom, are taken together with the carbon atom to which they are attached to form a carbonyl group; or two $R^2$ substituents, together with the carbon atoms to which they are attached, join to form a 3- to 6-membered saturated spiro-carbocyclic ring; $R^3$ is hydrogen or $C_{1-4}$ alkyl; $R^4$ is aryl wherein the aryl group is selected from the group consisting of: phenyl, naphthyl, pyridinyl, furyl, thienyl, pyrrolyl, oxazolyl, thiazolyl, imidazolyl, pyrazolyl, isoxazolyl, isothiazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, dihydrobenzofuryl, benzo(1,3)dioxolanyl, benzo(1,4)dioxanyl, and quinoxalinyl; and mono, di, and tri-substituted aryl wherein aryl is as defined above and the substituents are independently hydrogen, hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino-$C_{1-6}$ alkyl, $C_{1-6}$ alkylamino, di$(C_{1-6})$alkylamino, $C_{1-6}$ alkylamino-$C_{1-6}$ alkyl, di$(C_{1-6})$ alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl-$C_{1-6}$ alkyl, $C_{1-5}$ alkylcarbonyloxy, cyano, trifluoromethyl, 1,1,1-trifluoroethyl, trifluoromethoxy, trifluoroethoxy, or nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl; and $R^5$ is hydrogen or $C_{1-3}$ alkyl.

Compounds of Formula III as set forth in U.S. Patent Publication No. 20040019035 A1 including their various isomers, enantiomers, tautomers, racemates and polymorphs, or a pharmaceutically acceptable salt or ester thereof can be used in the methods of the invention:

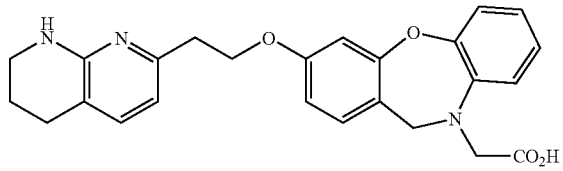

(III)

Compounds of Formula IV as set forth in U.S. Patent Publication No. 20040010023 A1 including their various isomers, enantiomers, tautomers, racemates and polymorphs, or a pharmaceutically acceptable salt or ester thereof can be used in the methods of the invention:

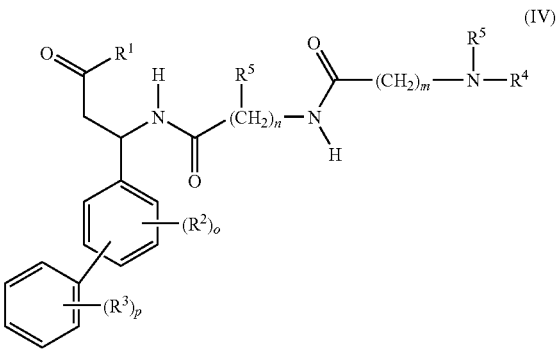

(IV)

in which $R^1$ is OR or $N(R)_2$, R is H, A, cycloalkyl, Ar, arylalkyl or Pol, $R^2$ and $R^3$ in each case independently of one another are H, A, Hal, $NO_2$, OR, $N(R)_2$, CN, CO—R, $SO_3R$, $SO_2R$, NH—C(O)A or SR, $R^4$ is a mono- or bicyclic aromatic heterocycle having 1 to 4 N atoms, which can be mono- or disubstituted by Hal, R, OR, CN, $N(R^5)_2$ or $NO_2$, where pyridine, pyridazine, pyrimidine, pyrazine, 1,3,5-, 1,2,4-, and 1,2,3-triazine and tetrazine are excluded, $R^5$ is H or A, $R^6$ is Hal or $NO_2$, A is alkyl having 1 to 8 C atoms, where the alkyl groups can be mono- or polysubstituted by $R^6$ and/or their alkyl carbon chain can be interrupted by —O—, Ar is aryl which is unsubstituted or mono-, di- or trisubstituted, cycloalkyl is cycloalkyl having 3 to 15 C atoms, Hal is F, Cl, Br or I, Pol is a solid phase without a terminal functional group, n, m in each case independently of one another are 1, 2, 3, 4, 5 or 6, o is 1, 2, 3 or 4, and p is 1, 2, 3, 4 or 5.

Compounds of Formula V as set forth in U.S. Patent Publication No. 20030181440 A1 including their various isomers, enantiomers, tautomers, racemates and polymorphs, or a pharmaceutically acceptable salt or ester thereof can be used in the methods of the invention:

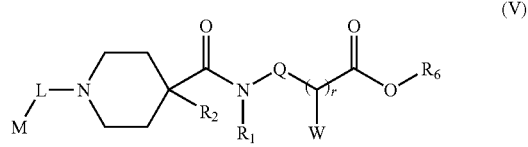

(V)

wherein M is selected from $C_1$-$C_4$ alkylene (optionally substituted within the carbon chain with one substituent selected from $C_1$-$C_4$ alkyl, $C_2$-$C_4$ alkenyl, cycloalkyl (wherein a ring carbon atom forms the point of attachment to the carbon chain) or aryl (optionally substituted with halogen) and substituted on the terminal carbon with one substituent selected from A), $C_2$-$C_4$ alkenylene (substituted with one substituent selected from A), heterocyclylene (optionally substituted with one substituent selected from A), heterocyclenylene (substituted with one substituent selected from A), arylene (substituted with one substituent selected from A), $(C_1$-$C_4$ alkylene)aryl (substituted on $C_1$-$C_4$ alkylene with one substituent selected from A) or arylene($C_1$-$C_4$)alkyl (substituted on arylene with one substituent selected from A);

A is optionally present and is selected from heteroaryl, heterocyclyl, $R_3$HN—, (heteroaryl)amino, (heterocyclyl) amino, $R_3$HNC(=NH)—, $R_3$HNC(=NH)NH—, $R_3$HNC(=O)NH—, $R_3$C(=NH)NH—, (heterocyclyl)aminooxy, (heteroaryl)aminooxy, $R_3$HNC(=NH)NHO—, $R_3$C(=NH)NHO—, $R_3$HNC(=NH)NHC=O)— or $R_3$C(=NH)NHC (=O)—; wherein heteroaryl and heterocyclyl are optionally substituted with one to five substituents independently selected from $C_1$-$C_4$ alkyl, $C_1$-$C_4$ alkoxy, heteroaryl (optionally substituted with $C_1$-$C_4$ alkyl), halogen, hydroxy, nitro, cyano, trihalo($C_1$-$C_4$)alkyl, $C_1$-$C_4$ alkylcarbonyl, $C_1$-$C_4$ alkoxycarbonyl, aryl($C_1$-$C_4$)alkoxycarbonyl, $R_3$HN—, amino($C_1$-$C_4$)alkyl, $C_1$-$C_4$ alkylamino($C_1$-$C_4$)alkyl or di($C_1$-$C_4$ alkyl)amino($C_1$-$C_4$)alkyl;

with the proviso that if A is $H_2NC(=NH)NH$—, then, dependently, W is not hydrogen when Q is —$CH_2$—;

L is selected from —C(=O)—, —$SO_2$—, —OC(=O)— or —HNC(=O)—; $R_1$ is selected from hydrogen, $C_1$-$C_8$ alkyl or cycloalkyl; $R_2$ is selected from hydrogen or $C_1$-$C_8$ alkyl; $R_3$ is selected from hydrogen, $C_1$-$C_8$ alkyl, aryl, aryl($C_1$-$C_8$)alkyl, cycloalkyl, hydroxy, cyano or nitro; Q is selected from —$CH_2$—, —CH($C_1$-$C_8$alkyl)-, —CH($C_2$-$C_8$alkenyl)-, —CH($C_2$-$C_8$alkynyl)-, —CH(aryl)- (wherein aryl is optionally substituted with one to five substituents independently selected from $C_1$-$C_4$ alkyl, $C_1$-$C_4$ alkoxy, —O—($C_1$-$C_3$ alkyl)-O—, halogen, hydroxy, trihalo($C_1$-$C_3$) alkyl or trihalo($C_1$-$C_3$)alkoxy), —CH(heteroaryl)- (wherein heteroaryl is optionally substituted with a substituent selected from halogen, hydroxy, $C_1$-$C_4$ alkyl, $C_1$-$C_4$ alkoxy, —O—($C_1$-$C_3$ alkyl)-O—, amino, $C_1$-$C_4$ alkylamino or di($C_1$-$C_4$) alkylamino) or —CH(aryl($C_1$-$C_8$)alkyl)-; W is selected from hydrogen or N($R_4$)T; r is an integer selected from 0 or 1; $R_4$ is selected from hydrogen, $C_1$-$C_8$ alkyl or $C_2$-$C_6$ acyl; T is selected from $R_5$C(=O)—, $R_5$OC(=O)— or $R_5$C(=N—CN)—; $R_5$ is selected from $C_1$-$C_8$ alkyl, aryl, aryl($C_1$-$C_8$) alkyl or amino (wherein amino is optionally substituted with one to two substituents independently selected from $C_1$-$C_8$ alkyl); $R_6$ is selected from hydrogen, $C_1$-$C_8$ alkyl, aryl($C_1$-$C_8$)alkyl, ($R_7$)N($C_1$-$C_8$)alkyl, ($R_8$)($R_7$)N($C_1$-$C_8$)alkyl or ($R_8$)($R_7$)NC(=O)—($C_1$-$C_8$)alkyl; and, $R_7$ and $R_8$ are independently selected from hydrogen, $C_1$-$C_8$ alkyl or cycloalkyl; and pharmaceutically acceptable salts thereof.

Compounds of Formula VI as set forth in U.S. Patent Publication No. 20030139398 A1 including their various isomers, enantiomers, tautomers, racemates and polymorphs, or a pharmaceutically acceptable salt or ester thereof can be used in the methods of the invention:

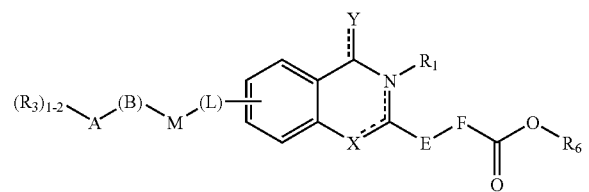

(VI)

wherein A is selected from the group consisting of carbonyl, amino, carbamoyl, acetamido, acetimido, amidino, iminomethylamino, ureido, biureto, biurea, thioureido, guanidino, biguanido, biguanidino, amidrazone, hydrazo, carbazoyl, semicarbazido, cycloalkylene, heterocyclene, arylene and heteroarylene; wherein arylene and heteroarylene are optionally substituted with one to two additional substituents independently selected from the group consisting of $C_1$-$C_8$ alkyl, $C_1$-$C_8$ alkoxy, halogen, (halo)$_{1-3}$($C_1$-$C_8$)alkyl and (halo)$_{1-3}$($C_1$-$C_8$)alkoxy; (B) is optionally present and is selected from the group consisting of NH, O and C(O); M is selected from the group consisting of $C_1$-$C_6$ alkylene, $C_2$-$C_6$ alkenylene, $C_2$-$C_6$ alkynylene and arylene; wherein arylene is optionally substituted with one to four additional substituents independently selected from the group consisting of $C_1$-$C_8$ alkyl, $C_1$-$C_8$ alkoxy, halogen, (halo)$_{1-3}$($C_1$-$C_8$)alkyl and (halo)$_{1-3}$($C_1$-$C_8$)alkoxy; $R_3$ is one to two substituents independently selected from the group consisting of hydrogen, $C_1$-$C_8$ alkyl, cycloalkyl, heterocyclo, aryl, aryl($C_1$-$C_8$)alkyl, heteroaryl, heteroaryl($C_1$-$C_8$)alkyl, amino, $C_1$-$C_8$ alkylamino, di($C_1$-$C_8$)alkylamino, imino, iminomethyl, amidino, $C_1$-$C_8$ alkylamidino, di($C_1$-$C_8$)alkylamidino, cycloalkylamidino, halogen and hydroxy; wherein cycloalkyl, heterocyclo, aryl, heteroaryl and the aryl and heteroaryl portions of arylalkyl and heteroarylalkyl are optionally substituted with one to two substituents independently selected from the group consisting of $C_1$-$C_8$ alkyl, $C_1$-$C_8$ alkoxy, aryl and halogen; and, wherein heterocyclo is optionally substituted with a substituent selected from oxo; (L) is optionally present and is selected from the group consisting of NH, O, S and C(O); Y is selected from the group consisting of two substituents joined to the ring by single-bonds and one substituent joined to the ring by a double-bond; wherein the two substituents joined to the ring by single-bonds are independently selected from the group consisting of hydrogen, $C_1$-$C_8$ alkyl, $C_1$-$C_8$ alkoxy, halogen, (halo)$_{1-3}$($C_1$-$C_4$)alkyl and (halo)$_{1-3}$($C_1$-$C_4$)alkoxy; alternatively, the two substituents are taken together to form a moiety selected from the group consisting of cycloalkyl and —O—($CH_2$)$_{1-4}$—O—; and, wherein the one substituent joined to the ring by a double-bond is selected from the group consisting of S, O, $C_1$-$C_8$ alkylidene, imino, ($C_1$-$C_4$)alkylimino, (halo)$_{1-2}$-methylene and (halo)$_{1-3}$($C_2$-$C_4$)alkylidene; X is selected from the group consisting of N, NH, O and S; $R_1$ is optionally present and is selected from the group consisting of hydrogen, $C_1$-$C_8$ alkyl, cycloalkyl, cycloalkyl($C_1$-$C_6$)alkyl, aryl, aryl($C_1$-$C_6$) alkyl, heteroaryl, heteroaryl($C_1$-$C_6$)alkyl, arylamino and heteroarylamino; wherein aryl, heteroaryl and the aryl and heteroaryl portions of arylalkyl and heteroarylalkyl are optionally substituted with one to five substituents independently selected from the group consisting of $C_1$-$C_8$ alkyl, $C_1$-$C_8$ alkoxy, aryl, aryl($C_1$-$C_8$)alkyl, heteroaryl, amino, $C_1$-$C_8$ alkylamino, di($C_1$-$C_8$ alkyl)amino, heteroarylamino, imino, iminomethyl, sulfonyl, halogen, hydroxy, nitro, cyano, (halo)$_{1-3}$($C_1$-$C_4$)alkyl and (halo)$_{1-3}$($C_1$-$C_4$)alkoxy; E is $C_1$-$C_4$ alkyl substituted with W and W'; F is $C_1$-$C_4$ alkyl substituted with U and U'; W, W', U and U' are independently selected from the group consisting of hydrogen, $C_1$-$C_8$ alkyl, $C_2$-$C_8$ alkenyl, $C_2$-$C_8$ alkynyl, cycloalkyl, cycloalkyl($C_1$-$C_4$) alkyl, heterocyclo, heterocyclo($C_1$-$C_4$)alkyl, aryl, aryl($C_1$-$C_4$)alkyl, biaryl, heteroaryl, heteroaryl($C_1$-$C_4$)alkyl, —N[($R_4$),T($R_5$)] and halogen; wherein heterocyclo, aryl, biaryl, heteroaryl and the heterocyclo, aryl and heteroaryl portions of heterocycloalkyl, arylalkyl and heteroarylalkyl are optionally substituted with one to five substituents independently selected from the group consisting of $C_1$-$C_4$ alkyl, $C_1$-$C_4$ alkoxy, amino, $C_1$-$C_4$ alkylamino, di($C_1$-$C_4$ alkyl) amino, halogen, hydroxy, nitro and cyano; and, alternatively, two optional substituents on aryl, heteroaryl and the aryl and heteroaryl portions of arylalkyl and heteroarylalkyl are taken together to form a moiety selected from the group consisting of cycloalkyl, heterocyclo and —O—($CH_2$)$_{1-4}$—O—; with the proviso that if one of W, W', U and U' are selected from —N[($R_4$),T($R_5$)], then the remaining W, W', U and U' cannot be selected from —N[($R_4$),T($R_5$)]; $R_4$ is selected from the group consisting of hydrogen and $C_1$-$C_8$ alkyl; T is selected from the group consisting of arylene, carbonyl, carboxyl, sulfonyl and —C(O)NH—; wherein arylene is optionally substituted with one to two additional substituents independently selected from the group consisting of $C_1$-$C_4$ alkyl, $C_1$-$C_4$ alkoxy and halogen; $R_5$ is selected from the group consisting of hydrogen, $C_1$-$C_8$ alkyl, $C_2$-$C_8$ alkenyl, cycloalkyl, heterocyclo, aryl, aryl($C_1$-$C_4$)alkyl, aryl($C_2$-$C_4$) alkenyl, biaryl, biaryl($C_1$-$C_4$)alkyl, heteroaryl, heteroaryl ($C_1$-$C_4$)alkyl and amino; wherein heterocyclo, aryl, heteroaryl and the aryl and heteroaryl portions of arylalkyl, arylalkenyl, biaryl, biarylalkyl and heteroarylalkyl are optionally substituted with one to five substituents independently selected from the group consisting of $C_1$-$C_4$ alkyl, $C_1$-$C_4$ alkoxy, heterocyclo, aryl, aryl($C_1$-$C_4$)alkyl, arylsulfonyl, heteroaryl, amino, $C_1$-$C_4$ alkylamino, di($C_1$-$C_4$ alkyl) amino, halogen, hydroxy, (halo)$_{1-3}$($C_1$-$C_4$)alkyl and (halo)$_{1-3}$($C_1$-$C_4$)alkoxy; and, alternatively, two optional substituents on aryl, heteroaryl and the aryl and heteroaryl portions of arylalkyl, arylalkenyl and heteroarylalkyl are taken together to form a moiety selected from the group consisting of cycloalkyl, heterocyclo and —O—(CH$_2$)$_{1-4}$—O—; $R_6$ is selected from the group consisting of hydrogen, $C_1$-$C_8$ alkyl and (CH$_2$)$_{1-8}$CON(R$_7$)$_2$; and, $R_7$ is selected from the group consisting of hydrogen, $C_1$-$C_8$ alkyl and cycloalkyl; and pharmaceutically acceptable racemates, enantiomers, diastereomers and salts thereof.

Compounds of Formula VII as set forth in U.S. Patent Publication No. 20020037889 A1 including their various isomers, enantiomers, tautomers, racemates and polymorphs, or a pharmaceutically acceptable salt or ester thereof can be used in the methods of the invention:

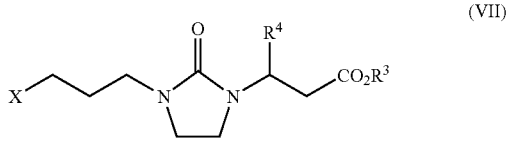

X is selected from the group consisting of

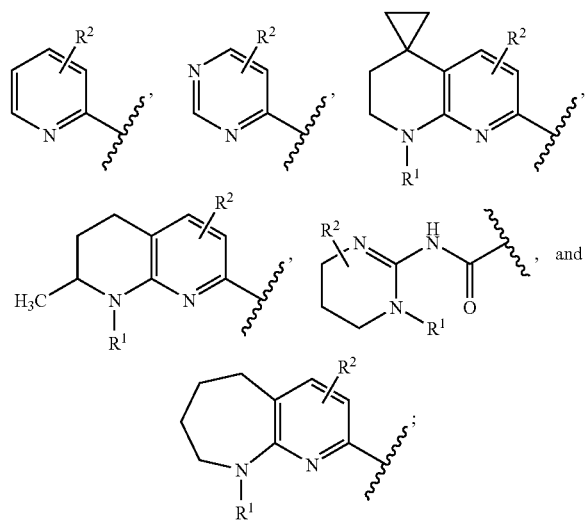

each $R^1$ is independently hydrogen or $C_{1-3}$ alkyl and each non-aromatic ring carbon atom is unsubstituted or independently substituted with one or two $R^2$ substituents and each aromatic ring carbon atom is unsubstituted or independently substituted with one $R^2$ substituent selected from the group consisting of: $C_{1-8}$ alkyl, $C_{3-8}$ cycloalkyl, $C_{3-8}$ cycloheteroalkyl, $C_{3-8}$ cycloalkyl-$C_{1-6}$ alkyl, $C_{3-8}$ cycloheteroalkyl-$C_{1-6}$ alkyl, aryl, aryl-$C_{1-6}$ alkyl, amino-$C_{1-6}$ alkyl, $C_{1-3}$ acylamino, $C_{1-3}$ acylamino-$C_{1-6}$ alkyl, amino, ($C_{1-6}$ alkyl)$_{1-2}$ amino, $C_{3-6}$ cycloalkyl-$C_{0-2}$ amino, ($C_{1-6}$ alkyl)$_{1-2}$ amino-$C_{1-6}$ alkyl, $C_{1-6}$ alkoxy, $C_{1-4}$ alkoxy-$C_{1-6}$ alkyl, hydroxycarbonyl, hydroxycarbonyl-$C_{1-6}$ alkyl, $C_{1-3}$ alkoxycarbonyl, $C_{1-3}$ alkoxycarbonyl-$C_{1-6}$ alkyl, hydroxy, hydroxy-$C_{1-6}$ alkyl, nitro, cyano, trifluoromethyl, trifluoromethoxy, trifluoroethoxy, $C_{1-8}$ alkyl-S(O)$_{0-2}$, ($C_{1-8}$ alkyl)$_{0-2}$ aminocarbonyl, $C_{1-8}$ alkyloxycarbonylamino, ($C_{1-8}$ alkyl)$_{1-2}$ aminocarbonyloxy, (aryl)$_{1-2}$ amino, aryl-$C_{1-3}$ alkylsulfonylamino, and $C_{1-8}$ alkylsulfonylamino; or two $R^2$ substituents, when on the same non-aromatic carbon atom, are taken together with the carbon atom to which they are attached to form a carbonyl group; or two $R^2$ substituents, together with the carbon atom to which they are attached, join to form a 3- to 6-membered saturated spiro-carbocyclic ring; $R^4$ is aryl wherein the aryl group is selected from the group consisting of: phenyl, naphthyl, pyridyl, furyl, thienyl, pyrrolyl, oxazolyl, thiazolyl, imidazolyl, pyrazolyl, isoxazolyl, isothiazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, dihydrobenzofuryl, benzo(1,3)dioxolanyl, and benzo(1,4)dioxanyl; and mono, di, and tri-substituted aryl wherein the substituents are independently hydrogen, hydroxy, hydroxy-$C_{1-6}$ alkyl, halogen, $C_{1-8}$ alkyl, $C_{3-8}$ cycloalkyl, aryl, aryl $C_{1-3}$ alkyl, amino, amino $C_{1-6}$ alkyl, $C_{1-3}$ acylamino, $C_{1-3}$ acylamino-$C_{1-6}$ alkyl, $C_{1-6}$ alkylamino, di($C_{1-6}$)alkylamino, $C_{1-6}$ alkylamino-$C_{1-6}$ alkyl, di($C_{1-6}$) alkylamino-$C_{1-6}$ alkyl, $C_{1-4}$ alkoxy, $C_{1-4}$ alkylthio, $C_{1-4}$ alkylsulfinyl, $C_{1-4}$ alkylsulfonyl, $C_{1-4}$ alkoxy-$C_{1-6}$ alkyl, hydroxycarbonyl, hydroxycarbonyl-$C_{1-6}$ alkyl, $C_{1-5}$ alkoxycarbonyl, $C_{1-3}$ alkoxycarbonyl-$C_{1-6}$ alkyl, $C_{1-5}$ alkylcarbonyloxy, cyano, trifluoromethyl, 1,1,1-trifluoroethyl, trifluoromethoxy, trifluoroethoxy, or nitro; or two adjacent substituents together with the carbon atoms to which they are attached join to form a five- or six-membered saturated or unsaturated ring containing 1 or 2 heteroatoms selected from the group consisting of N, O, and S, whose ring carbon atoms may be substituted with oxo or $C_{1-3}$ alkyl; and $R^3$ is hydrogen or $C_{1-3}$ alkyl.

Compounds of Formula VIII as set forth in U.S. Patent Publication No. 20020077321 A1 including their various isomers, enantiomers, tautomers, racemates and polymorphs, or a pharmaceutically acceptable salt or ester thereof can be used in the methods of the invention:

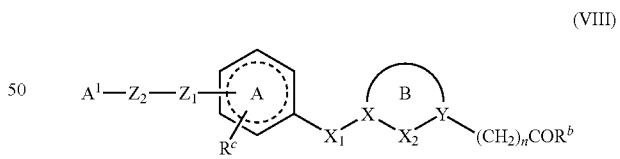

wherein

is a 4-8 membered monocyclic ring or a 7-12 membered bicyclic ring, which ring is optionally saturated or unsaturated; which ring is optionally substituted with one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, alkylsulfone, sulfonamide, allyl, alkenyl, methylenedioxy, ethylenedioxy, alkynyl, carboxamide, cyano, and —(CH$_2$)$_n$COR wherein n is 0-2 and R is hydroxy, alkoxy, alkyl or amino;

A$^1$ is a 5-9 membered monocyclic ring or 7-12 membered bicyclic heterocycle ring of the formula

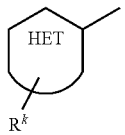

containing at least one nitrogen atom and optionally containing 1 to 4 heteroatoms, selected from the group consisting of O, N, S, SO$_2$ and CO; optionally saturated or unsaturated; optionally substituted by one or more R$^k$ is selected from the group consisting of hydroxy, alkyl, alkoxy, alkoxyalkyl, thioalkyl, cyano, amino, alkylamino, haloalkyl, halogen, acylamino, sulfonamide and —COR wherein R is hydroxy, alkoxy, alkyl or amino;

or A$^1$ is

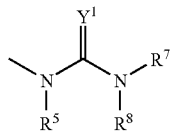

wherein Y$^1$ is selected from the group consisting of N—R$^2$, O, and S; R$^2$ is selected from the group consisting of H; alkyl; aryl; hydroxy; alkoxy; cyano; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl; R$^2$ taken together with R$^7$ forms a 4-12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester; or R$^2$ taken together with R$^7$ forms a 4-12 membered heterocycle containing one or more heteroatom selected from O, N and S optionally unsaturated; or R$^2$ taken together with R$^7$ forms a 5 membered heteroaromatic ring fused with a aryl or heteroaryl ring; R$^7$ (when not taken together with R$^2$) and R$^8$ are independently selected from the group consisting of H; alkyl; aralkyl; amino; alkylamino; hydroxy; alkoxy; arylamino; amido, alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl; or NR$^7$ and R$^8$ taken together form a 4-12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S; R$^5$ is selected from the group consisting of H, and alkyl;

or A is

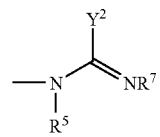

wherein Y is selected from the group consisting of alkyl; cycloalkyl; bicycloalkyl; aryl; monocyclic heterocycles; Z$_1$ is selected from the group consisting of CH$_2$, CH$_2$O, O, NH, NR$_k$, CO, S, SO, CH(OH), and SO$_2$, wherein R$_k$ is selected from H or lower alkyl; Z$_2$ is a 1-5 carbon linker optionally containing one or more heteroatom selected from the group consisting of O, S and N; alternatively Z$_1$-Z$_2$ may further contain a carboxamide, sulfone, oxime, sulfonamide, alkenyl, alkynyl, or acyl group; wherein the carbon and nitrogen atoms of Z$_1$-Z$_2$ are optionally substituted by alkyl, alkoxy, thioalkyl, alkylsulfone, aryl, alkoxyalkyl, hydroxy, alkylamino, heteroaryl, alkenyl, alkynyl, carboxyalkyl, halogen, haloalkyl or acylamino;

wherein Z$_2$-Z$_1$ is attached to

at the para or meta position relative to the X$_1$ substituent; n is an integer 0, 1 or 2; R$^c$ is selected from the group consisting of hydrogen; alkyl; halogen, hydroxy, nitro, alkoxy, amino, haloalkyl, aryl, heteroaryl, alkoxyalkyl, aminoalkyl, hydroxyalkyl, thioalkyl, alkylamino, arylamino, alkylsulfonylamino, acyl, acylamino, sulfonyl, sulfonamide, allyl, alkenyl, methylenedioxy, ethylenedioxy, alkynyl, alkynylalkyl, carboxy, alkoxycarbonyl, carboxamido, cyano, and —(CH$_2$)$_n$—COR wherein n is 0-2 and R is selected from hydroxy, alkoxy, alkyl and amino; X$_1$ is selected from the group consisting of —O—, CO, SO$_2$, NR$^m$ and (CHR$^p$)$_q$; wherein R$^m$ is H or alkyl; R$^p$ is H, alkyl, alkoxy or hydroxy and q is 0 or 1; X$_2$ is selected from the group consisting of —CHR$^e$—, CO, SO$_2$, O, NR$^f$ and S; R$^e$ is selected from the group consisting of H, alkyl, hydroxy and alkoxy; R$^f$ is H or alkyl; X or Y are independently selected from the group consisting of —CR$^g$— or —N— wherein R$^g$ is selected from the group consisting of H, alkyl, haloalkyl, fluoro, alkoxyalkyl, alkynyl, aryl, heteroaryl, aralkyl, alkylsulfone, heteroaralkyl, hydroxy, alkoxy, hydroxyalkyl, and carboxyalkyl; the group X—X$_2$—Y optionally contains a moiety selected from the group consisting of acyl, alkyl, amino, ether, thioether, sulfone, and olefin;

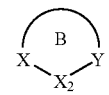

forms a 3-8 membered monocyclic ring system; or an 8-11 membered bicyclic system; optionally saturated or unsaturated; the monocyclic ring system optionally containing 1-2 heteroatoms selected from N, O and S; the bicyclic ring system optionally containing 1-4 heteroatoms selected from N, O, S or optionally containing the group such as SO$_2$ or CO); and optionally substituted with one or more substituent selected from the group consisting of alkyl, halogen, cyano, carboalkoxy, haloalkyl, alkoxyalkyl, alkylsulfone, aryl, heteroaryl, aralkyl, heteroaralkyl or alkoxy; $R^b$ is $X_3—R^h$ wherein $X_3$ is selected from the group consisting of O, S and $NR^j$ wherein $R^h$ and $R^j$ are independently selected from the group consisting of H, alkyl, acyl, aryl, aralkyl and alkoxyalkyl; and n is 0, 1 or 2.

In addition, compounds of Formula IX or Formula X as set forth in U.S. Patent Publication No. 20020072500 including their various isomers, enantiomers, tautomers, racemates and polymorphs, or a pharmaceutically acceptable salt or ester thereof can be used in the methods of the invention:

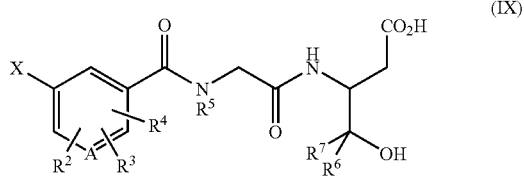

(IX)

wherein

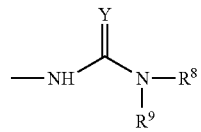

X is

Y is selected from the group consisting of N—$R^1$, O, and S; A is N or C; $R^1$ is selected from the group consisting of H, alkyl, aryl, hydroxy, alkoxy, cyano, nitro, amino, alkenyl, alkynyl, amido, alkylcarbonyl, arylcarbonyl, alkoxycarbonyl, aryloxycarbonyl, haloalkylcarbonyl, haloalkoxycarbonyl, alkylthiocarbonyl, arylthiocarbonyl, acyloxymethoxycarbonyl, alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles, aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle, monocyclic heterocycles, and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^1$ taken together with $R^8$ forms a 4-12 membered dinitrogen containing heterocycle optionally substituted with one or more substituent selected from the group consisting of lower alkyl, hydroxy, keto, alkoxy, halo, phenyl, amino, carboxyl or carboxyl ester, and fused phenyl; or $R^1$ taken together with $R^8$ forms a 5 membered heteroaromatic ring optionally substituted with one or more substituent selected from lower alkyl, phenyl and hydroxy; or $R^1$ taken together with $R^8$ forms a 5 membered heteroaromatic ring fused with a phenyl group; $R^8$ (when not taken together with $R^1$) and $R^9$ are independently selected from the group consisting of H, alkyl, alkenyl, alkynyl, aralkyl, amino, alkylamino, hydroxy, alkoxy, arylamino, amido, alkylcarbonyl, arylcarbonyl, alkoxycarbonyl, aryloxy, aryloxycarbonyl, haloalkylcarbonyl, haloalkoxy-carbonyl, alkylthiocarbonyl, arylthiocarbonyl, acyloxymethoxycarbonyl, cycloalkyl, bicycloalkyl, aryl, acyl, benzoyl, alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles, monocyclic heterocycles, monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl, monocyclic and bicyclic heterocyclicalkyls, —$SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

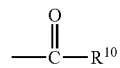

wherein $R^{10}$ is defined as above; or $NR^8$ and $R^9$ taken together form a 4-12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

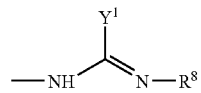

X is or wherein $Y^1$ is selected from the group consisting of alkyl, cycloalkyl, bicycloalkyl, aryl, monocyclic heterocycles, alkyl optionally substituted with aryl which can also be optionally substituted with one or more substituent selected from halogen, haloalkyl, alkyl, nitro, hydroxy, alkoxy, aryloxy, aryl, or fused aryl, aryl optionally substituted with one or more substituent selected from halogen, haloalkyl, hydroxy, alkoxy, aryloxy, aryl, fused aryl, nitro, methylenedioxy, ethylenedioxy, or alkyl, alkynyl, alkenyl, —S—$R^{11}$ and —$OR^{11}$ wherein $R^{11}$ is selected from the group consisting of H, alkyl, aralkyl, aryl, alkenyl, and alkynyl, or $R^{11}$ taken together with $R^8$ forms a 4-12 membered mononitrogen and monosulfur or monooxygen containing heterocyclic ring optionally substituted with lower alkyl, hydroxy, keto, phenyl, carboxyl or carboxyl ester, and fused phenyl, or $R^{11}$ taken together with $R^8$ is thiazole, oxazole, benzoxazole, or benzothiazole; $R^8$ is defined as above; or $Y^1$ (when $Y^1$ is carbon) taken together with $R^8$ forms a 4-12 membered mononitrogen or dinitrogen containing ring optionally substituted with alkyl, aryl, keto or hydroxy; or X is

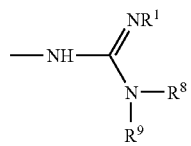

wherein $R^1$ and $R^8$ taken together form a 5-8 membered dinitrogen containing heterocycle optionally substituted with one or more substituent selected from the group consisting of lower alkyl, hydroxy, keto, phenyl, or carboxyl derivatives; and $R^9$ is selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl, or acyloxymethoxycarbonyl; or X is

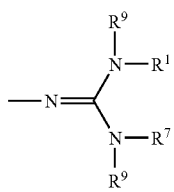

wherein $R^1$ and $R^8$ taken together form a 5-8 membered dinitrogen containing heterocycle optionally substituted with hydroxy, keto, phenyl, or alkyl; and $R^9$ are both selected from the group consisting of alkylcarbonyl, arylcarbonyl, alkoxycarbonyl, aryloxycarbonyl, haloalkylcarbonyl, haloalkoxycarbonyl, alkylthiocarbonyl, arylthiocarbonyl and acyloxymethoxycarbonyl; $R^2$, $R^3$ and $R^4$ are independently selected from one or more substituent selected from the group consisting of H, alkyl, hydroxy, alkoxy, aryloxy, halogen, haloalkyl, haloalkoxy, nitro, amino, alkylamino, acylamino, dialkylamino, cyano, alkylthio, alkylsulfonyl, carboxyl derivatives, trihaloacetamide, acetamide, aryl, fused aryl, cycloalkyl, thio, monocyclic heterocycles, fused monocyclic heterocycles, and X, wherein X is defined as above; $R^5$, $R^6$ and $R^7$ are independently selected from the group consisting of hydrogen, alkyl, alkenyl, alkynyl, aryl, carboxyl derivatives, haloalkyl, cycloalkyl, monocyclic heterocycles, monocyclic heterocycles optionally substituted with alkyl, halogen, haloalkyl, cyano, hydroxy, aryl, fused aryl, nitro, alkoxy, aryloxy, alkylsulfonyl, arylsulfonyl, sulfonamide, thio, alkylthio, carboxyl derivatives, amino, amido, alkyl optionally substituted with one or more of halo, haloalkyl, hydroxy, alkoxy, aryloxy, thio, alkylthio, alkynyl, alkenyl, alkyl, arylthio, alkylsulfoxide, alkylsulfonyl, arylsulfoxide, arylsulfonyl, cyano, nitro, amino, alkylamino, dialkylamino, alkylsulfonamide, arylsulfonamide, acylamide, carboxyl derivatives, sulfonamide, sulfonic acid, phosphonic acid derivatives, phosphinic acid derivatives, aryl, arylthio, arylsulfoxide, or arylsulfone all optionally substituted on the aryl ring with halo, alkyl, haloalkyl, cyano, nitro, hydroxy, carboxyl derivatives, alkoxy, aryloxy, amino, alkylamino, dialkylamino, amido, aryl, fused aryl, monocyclic heterocycles, and fused monocyclic heterocycles, monocyclic heterocyclicthio, monocyclic heterocyclicsulfoxide, and monocyclic heterocyclic sulfone, which can be optionally substituted with halo, haloalkyl, nitro, hydroxy, alkoxy, fused aryl, or alkyl, alkylcarbonyl, haloalkylcarbonyl, and arylcarbonyl, aryl optionally substituted in one or more positions with halo, haloalkyl, alkyl, alkoxy, aryloxy, methylenedioxy, ethylenedioxy, alkylthio, haloalkylthio, thio, hydroxy, cyano, nitro, acyloxy, carboxyl derivatives, carboxyalkoxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles and fused monocyclic heterocycles.

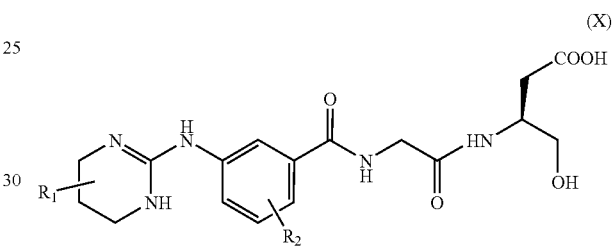

(X)

wherein $R_1$ and $R_2$ are selected from a group consisting of hydrogen, hydroxy alkyl haloalkyl and halo.

Compounds of Formula XI, XII, XIII, XIV, XV, XVI, XVII, XVIII, XIX, and XX as set forth in Goodman et al., *J. Med. Chem.* 45 (5):1045-51 (2002) including their various isomers, enantiomers, tautomers, racemates and polymorphs, or a pharmaceutically acceptable salt or ester thereof can be used in the methods of the invention:

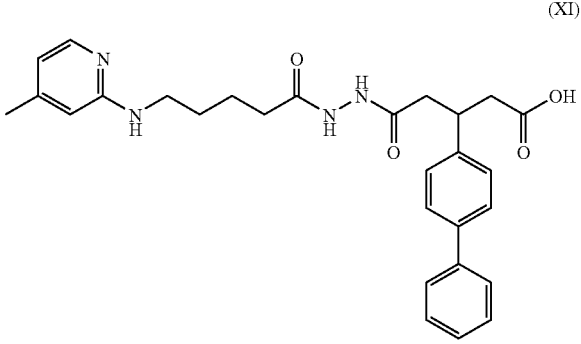

(XI)

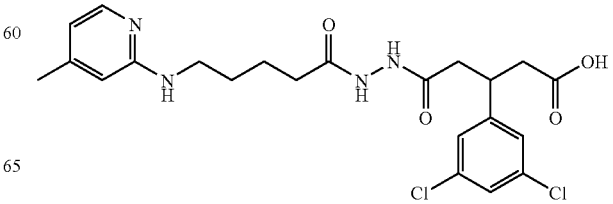

(XII)

-continued (XIII)
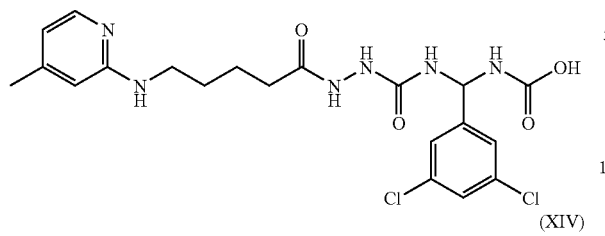

(XIV)
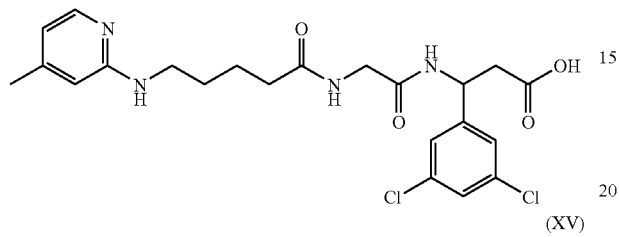

(XV)
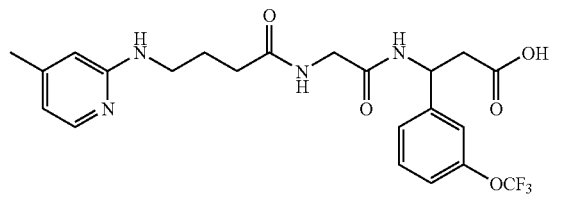

(XVI)
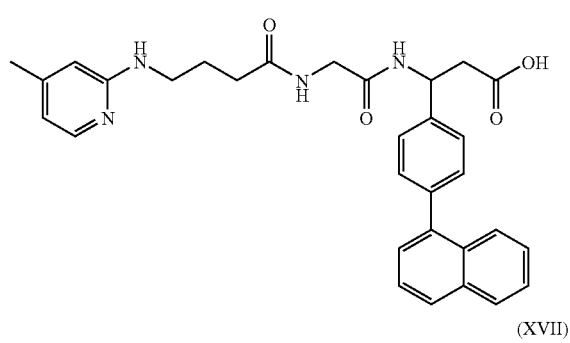

(XVII)
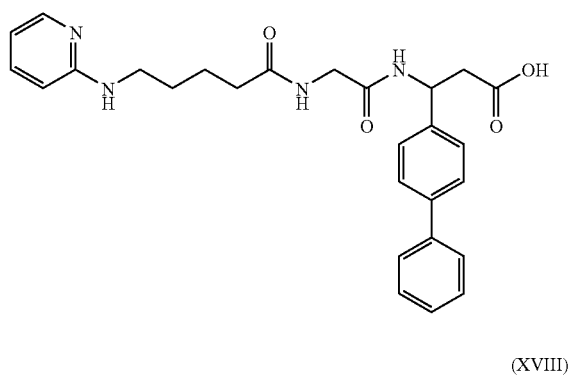

(XVIII)
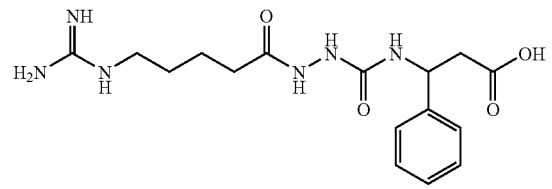

-continued (XIX)
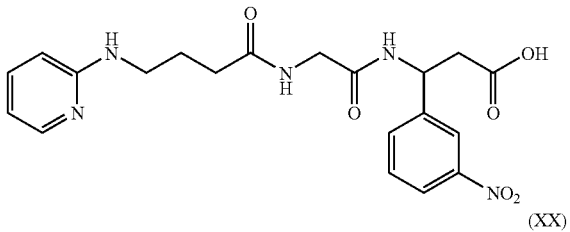

(XX)
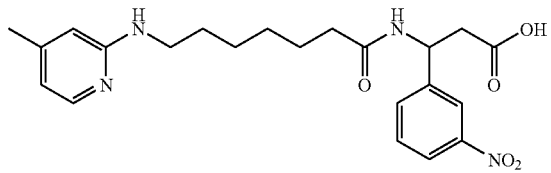

In some cases, the αvβ5 antagonists of the invention will comprise the tri-peptide sequence RGD. The design of such molecules as ligands for the integrins is exemplified, for example, in Pierschbacher et al., *J. Cell. Biochem.* 56:150-154 (1994)); Ruoslahti, *Ann. Rev. Cell. Dev. Bio.* 12:697-715 (1996); Chorev et al. *Biopolymers* 37:367-375 (1995)); Pasqualini et al., *J. Cell. Biol.* 130:1189-1196 (1995)); Smith et al., *J. Biol. Chem.* 269:32788-32795 (1994); and U.S. Pat. Nos. 5,780,426 and 6,683,051.

C. Inhibiting Expression of αvβ5 Integrin

As discussed above, the present invention is based on the surprising discovery that blocking binding of ligands to αvβ5 integrin reduces the severity of PE. For example, as described in Example 3 below, the present inventors have demonstrated that β5$^{-/-}$ mice do not develop PE associated with lung injury. Therefore, a nucleotide sequence that interferes with the specific expression of the αvβ5 integrin gene at the transcriptional or translational level can be used to treat or prevent PE. This approach may utilize, for example, siRNA and/or antisense oligonucleotides to block transcription or translation of a specific mutated mRNA, either by inducing degradation of the mRNA with a siRNA or by masking the mRNA with an antisense nucleic acid.

1. siRNA

Double stranded siRNA that corresponds to the β gene, can be used to silence the transcription and/or translation of αvβ5 integrin by inducing degradation of β5 mRNA transcripts, and thus treat or prevent PE by preventing expression of αvβ5 integrin. The siRNA is typically about 5 to about 100 nucleotides in length, more typically about 10 to about 50 nucleotides in length, most typically about 15 to about 30 nucleotides in length. siRNA molecules and methods of generating them are described in, e.g., Bass, 2001, *Nature*, 411, 428-429; Elbashir et al., 2001, *Nature*, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, *Molecular Interventions,* 2:158 (2002). For example, dsRNA oligonucleotides that specifically hybridize to the nucleic acid sequences set forth in Genbank Accession Nos.: AK054968; BF588784; BE208820; BE207859; or BE206567 can be used in the methods of the present invention. A decrease in the severity of PE symptoms in comparison to symptoms detected in the absence of the interfering RNA can be used to monitor the efficacy of the siRNA.

siRNA can be delivered to the subject using any means known in the art, including by injection, inhalation, or oral ingestion of the siRNA. Another suitable delivery system for siRNA is a colloidal dispersion system such as, for example, macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. Nucleic acids, including RNA and DNA within liposomes and be delivered to cells in a biologically active form (Fraley, et al., *Trends Biochem. Sci.,* 6:77, 1981). Liposomes can be targeted to specific cell types or tissues using any means known in the art.

2. Antisense Oligonucleotides

Antisense oligonucleotides that specifically hybridize to nucleic acid sequences encoding β5 polypeptides can also be used to silence the transcription and/or translation of αvβ5 integrin, and thus treat or prevent PE. For example, antisense oligonucleotides that specifically hybridize to the nucleic acid sequences set forth in Genbank Accession Nos.: BF588784; BE208820; BE207859; BE206567; NM_002213; BC006541; NM_174679; AF468059; AY434090; NM_010580; BC058246; XM_147237; AF022111; AF022110; AF043257; AF043256; and S58644 can be used in the methods of the present invention. A decrease in the severity of PE symptoms in comparison to symptoms detected in the absence of the antisense nucleic acids can be used to monitor the efficacy of the antisense nucleic acids.

Antisense nucleic acids are DNA or RNA molecules that are complementary to at least a portion of a specific mRNA molecule (see, e.g., Weintraub, *Scientific American,* 262:40 (1990)). Typically, synthetic antisense oligonucleotides are generally between 15 and 25 bases in length. Antisense nucleic acids may comprise naturally occurring nucleotides or modified nucleotides such as, e.g., phosphorothioate, methylphosphonate, and -anomeric sugar-phosphate, backbone-modified nucleotides.

In the cell, the antisense nucleic acids hybridize to the corresponding mRNA, forming a double-stranded molecule. The antisense nucleic acids, interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target nucleotide mutant producing cell. The use of antisense methods to inhibit the in vitro translation of genes is well known in the art (Marcus-Sakura, *Anal. Biochem.,* 172:289, (1988)). Less commonly, antisense molecules which bind directly to the DNA may be used.

Delivery of antisense polynucleotides specific for αvβ5 integrin genes can be achieved using any means known in the art including, e.g., direct injection, inhalation, or ingestion of the polynucleotides. In addition, antisense polynucleotides can be delivered using a recombinant expression vector (e.g., a viral vector based on an adenovirus, a herpes virus, a vaccinia virus, or a retrovirus) or a colloidal dispersion system (e.g., liposomes) as described herein. Various viral vectors that can be utilized for gene therapy as taught herein include IV. Identifying Additional αvβ5 Antagonists Additional antagonists of αvβ5 integrin can be readily identified according to methods well known to those of skill in the art. One convenient method for screening for antagonists involves measuring the ability of the potential antagonists to compete for binding of a known ligand of the integrin. For example, vitronectin, fibronectin, osteopontin, tenascin c and adenovirus penton base are known ligands of αvβ5 integrin that can be used in competition assays to identify potential antagonists of αvβ5 integrin. Other polypeptides comprising the amino acid sequence RGD can also be used in competition assays. In addition, monoclonal antibodies and fragments thereof that bind to αvβ5 integrin can be used to screen for additional antagonists of αvβ5 integrin. In some embodiments, ALULA and antibodies that compete with ALULA for binding to αvβ5 are used to screen for additional antagonists of αvβ5 integrin.

Competition assays are well known in the art. Typically, a ligand of αvβ5 integrin or an antibody that competes for ligand binding to αvβ5 integrin (e.g., ALULA) is labeled so that differences in binding to αvβ5 integrin (e.g., in the presence of increasing amount of a potential competing ligand for αvβ5 integrin) can be measured. The ligands may be naturally occurring ligands as well as synthetic ligands. Competition assays indicate the affinity of potential competitor antagonists.

A number of different screening protocols can be utilized to identify agents that modulate the level of activity or function of a particular topology of αvβ5 integrin in cells, e.g., in mammalian cells, and especially in human cells. In general terms, the screening methods involve screening a plurality of agents to identify an agent that interacts with αvβ5, for example, by binding to αvβ5 integrin or preventing an antibody (e.g., ALULA) or ligand specific for αvβ5 integrin (e.g., vitronectin, fibronectin, osteopontin, tenascin c, adenovirus penton base) from binding to αvβ5 integrin.

Preliminary screens can be conducted by screening for agents capable of binding to αvβ5 integrin, as at least some of the agents so identified are likely αvβ5 integrin antagonists. The binding assays usually involve contacting αvβ5 integrin with one or more test agents and allowing sufficient time for αvβ5 integrin and test agents to form a binding complex. Any binding complexes formed can be detected using any of a number of established analytical techniques. Protein binding assays include, but are not limited to, immunohistochemical binding assays, flow cytometry or other assays. The αvβ5 integrin utilized in such assays can be naturally expressed, cloned or synthesized.

The screening methods of the invention can be performed as in vitro or cell-based assays. Cell based assays can be performed in any cells in which αvβ5 integrin is expressed. Cell-based assays may involve whole cells or cell fractions containing αvβ5 integrin to screen for agent binding or modulation of αvβ5 integrin activity by the agent. One of skill in the art will appreciate that αvβ5 integrin can be expressed in cells that do not contain endogenous αvβ5 integrin. Suitable cell-based assays are described in, e.g., DePaola et al., *Annals of Biomedical Engineering* 29:1-9 (2001).

Agents that are initially identified as interacting with αvβ5 integrin can be further tested to validate the apparent activity. Preferably such studies are conducted with suitable cell-based or animal models of PE as described in Example 1 below. The basic format of such methods involves administering a lead compound identified during an initial screen to an animal that serves as a model and then determining if in fact the PE is ameliorated. The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like).

The agents tested as potential antagonists of αvβ5 integrin can be any small chemical compound, or a biological entity, such as a polypeptide, sugar, nucleic acid or lipid. Alternatively, modulators can be genetically altered versions of αvβ5 integrin or an αvβ5 integrin ligand. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays).

In some embodiments, the agents have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5H-bond donors (expressed as the sum of OHs and NHs); having a molecular weight over 500; having a LogP over 5 (or MLogP over 4.15); and/or having more than 10H-bond acceptors (expressed as the sum of Ns and Os). See, e.g., Lipinski et al. *Adv Drug Delivery Res* 23:3-25 (1997). Compound classes that are substrates for biological transporters are typically exceptions to the rule.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14 (3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., ECIS™, Applied BioPhysics Inc., Troy, N.Y., MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

V. Therapeutic Treatment

As discussed above, the invention also provides compositions comprising antagonists of αvβ5 integrin. The compositions of the invention can be provided to treat or prevent diseases which involve αvβ5 integrins including, e.g., PE, stroke, myocardial infarction, and cancer (i.e., angiogenesis).

In one embodiment, the compositions of the invention (e.g., compositions comprising ALULA, humanized ALULA, or ALULA fragments) can be provided to treat or prevent PE in subjects with PE or at risk for developing PE. For example, a subject having had exposure to a toxic inhalant would likely be treated after such exposure, whereas a patient at risk of PE can be treated prophylactically and/or therapeutically. Examples of patients at risk of PE include patients with acute aspiration, patients exhibiting symptoms of bacterial sepsis, patients whose blood cultures are positive for gram positive or gram negative bacteria, patients with pancreatitis, or patients in hemorrhagic shock.

The compositions of the invention may be administered on a regular basis (e.g., daily) for a period of time (e.g., 2, 3, 4, 5, 6, days or 1-3 weeks or more).

The compositions of the invention can be administered directly to the mammalian subject to block αvβ5 binding using any route known in the art, including e.g., by injection (e.g., intravenous, intraperitoneal, subcutaneous, intramuscular, or intradermal), inhalation, transdermal application, rectal administration, or oral administration.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed., 1989).

The compositions of the invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part a of prepared food or drug.

Formulations suitable for oral administration can comprise: (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The dose administered to a patient, in the context of the present invention should be sufficient to effect a beneficial response in the subject over time, e.g., a reduction in pulmonary capillary hydrostatic pressure, a reduction in fluid in the lungs, a reduction in the rate of fluid accumulation in the lungs, or a combination thereof. The optimal dose level for any patient will depend on a variety of factors including the efficacy of the specific modulator employed, the age, body weight, physical activity, and diet of the patient, on a possible combination with other drugs, and on the severity of the PE. The size of the dose also will be determined by the existence, nature, and extent of any adverse side-effects that accompany the administration of a particular compound or vector in a particular subject.

In determining the effective amount of the antagonists of αvβ5 integrin to be administered a physician may evaluate circulating plasma levels of the antagonist and antagonist toxicity. In general, the dose equivalent of an antagonist is from about 1 ng/kg to 10 mg/kg for a typical subject.

For administration, the antagonists of αvβ5 integrin can be administered at a rate determined by the $LD_{50}$ of the antagonist, and the side-effects of the antagonist at various concentrations, as applied to the mass and overall health of the subject. Administration can be accomplished via single or divided doses.

VI. Combination Therapy

In some embodiments, an antagonist of αvβ5 integrin is administered in conjunction with a second therapeutic agent for treating or preventing a disease or disorder associated with αvβ5 integrin (e.g., stroke, myocardial infarction, and cancer (i.e., angiogenesis)). For example, an antagonist of αvβ5 integrin may be administered in conjunction with a second therapeutic agent for treating or preventing acute lung injury and/or ARDS or PE. For example, an antagonist of αvβ5 integrin (e.g., ALULA, humanized ALULA, or fragments of ALULA) may be administered in conjunction with any of the standard treatments for PE including, e.g., diuretic agents, bronchodilating agents, narcotics, oxygen, and selective tourniquet application. In addition, an antagonist of αvβ5 integrin may be administered in conjunction with agents that target metabolic pathways that are implicated in acute lung injury and/or ARDS or PE. For example, an antagonist of αvβ5 integrin may be administered in conjunction with TGFβ pathway inhibitors, activated Protein C, steroids, GM-CSF, platelet inhibitors, β-2 agonists, surfactants, antibodies that specifically bind to αvβ5 integrin or β5, a second antagonist of αvβ5 integrin, antibodies that specifically bind to a αvβ6 integrin, antagonists of αvβ6 integrin, thrombin receptor antagonists, anti-thrombin agents, rho kinase inhibitors, and nucleic acids that inhibit expression of αvβ5 integrin including e.g., the antisense oligonucleotides and siRNA described herein. Suitable TGFβ pathway inhibitors include, e.g., TGF-β antibodies (including those that specifically block TGF-β1, TGF-β2, TGF-β3 or any combination thereof) as described in e.g., Ling et al, *J. Amer. Soc. Nephrol.* 14: 377-388 (2003), McCormick et al., *J. Immunol.* 163:5693-5699 (1999), and Cordeiro, *Curr. Opin. Mol. Ther.* 5 (2):199-203 (2003); TGF-β receptor type II inhibitors or TGF-β receptor type I kinase inhibitors as described in, e.g., DaCosta Bayfield, *Mol. Pharmacol.* 65 (3):744-52 (2004), Laping, *Curr. Opin. Pharmacol.* 3 (2):204-8 (2003), Laping, *Mol. Pharmacol.* 62 (1):58-64 (2002); soluble TGF-β receptor type II as described in, e.g., Pittet, *J. Clin. Invest.* 107:1537-1544 (2001); Wang et al., *Exp Lung Res.* 28 (6):405-17 (2002) and Wang, *Thorax* 54 (9):805-12 (1999); soluble latency associated peptides as described in, e.g., Zhang, *J. Invest. Dermatol.* 121 (4):713-9 (2003); thrombospondin I inhibitors as described in, e.g., Crawford et al., *Cell* 93:1159-1170 (1998), Riberiro et al., *J. Biol. Chem.* 274:13586-13593 (1999), and Schultz-Cherry et al., *J. Biol. Chem.* 269: 26775-26782 (1994). Suitable β-2 agonists include, e.g., albuterol, bitolterol, formoterol, isoproterenol, levalbuterol, metaproterenol, pirbuterol, salmeterol, and terbutaline. Suitable surfactants include, e.g., exosurf, infasurf, KL-4, pumactant, survanta, venticute, and surfactant TA, as described in Taeusch et al., *Acta Pharmacol Sin* 23 Supplement: 11-15 (2002). Suitable anti-thrombin agents include, e.g., hirudin, Hirulog (Biogen), argatroban (Texas Biotechnology) and efegatran (Lilly) and compounds described in U.S. Pat. No. 6,518,244. Suitable thrombin receptor antagonists are described in, e.g., U.S. Pat. Nos. 6,544,982; 6,515,023; 6,403,612; 6,399,581; and 5,446,131. Suitable rho kinase inhibitors include, e.g., Y-27632 as described in e.g., Tasaka et al, *Am J Respir Cell Mol. Biol.* 2005 Mar. 18; [Epub ahead of print], fasudil as described in, e.g., Nishikimi et al, *J Hypertens.* 22 (9):1787-96 (2004), 1-(5-isoquinolinesulfonyl)-homopiperazine (HA-1077), (S)-(+)-2-methyl-1-[(4-methyl-5-isoquinoline)sulfonyl]-homopiperazine (H-1152P) as described in, e.g., Sasaki et al., *Pharmacol Ther.* 93 (2-3):225-32 (2002), and additional rho kinase inhibitors as described in, e.g., U.S. Pat. Nos. 6,451,825 and 6,218,410 and U.S. Patent Publication Nos. 20050014783 and 20030134775.

In addition, the antagonist of αvβ5 integrin may be administered combination with an adenovirus expressing ATPase as described in U.S. Patent Publication No. 20020192186; with a β2 adrenergic receptor as described in U.S. Patent Publication No. 20020004042; with VEGFβ antagonists as described in U.S. Pat. No. 6,284,751; with lipid peroxidation inhibitors as described in U.S. Pat. No. 5,231,114; and with small molecule inhibitors for αvβ6, αvβ5, and αvβ3 integrins as described in, e.g., US Published Patent Application Nos. 2000/40019206, 2004/0019037, 2004/0019035, 2004/0018192, 2004/0010023, 2003/0181440, 2003/0171271, 2003/0139398, 2002/0037889, 2002/0077321, 2002/0072500, U.S. Pat. No. 6,683,051 and Goodman et al., *J. Med Chem.* 45 (5):1045-51 (2002).

The antagonist of αvβ5 integrin (e.g., ALULA, humanized ALULA, or fragments of ALULA) and the second therapeutic agent may be administered simultaneously or sequentially. For example, the antagonist of αvβ5 integrin may be administered first, followed by the second therapeutic agent. Alternatively, the second therapeutic agent may be administered first, followed by the antagonist of αvβ5 integrin. In some cases, the antagonist of αvβ5 integrin and the second therapeutic agent are administered in the same formulation. In other cases the antagonist of αvβ5 integrin and the second therapeutic agent are administered in different formulations. When the antagonist of αvβ5 integrin and the second therapeutic agent are administered in different formulations, their administration may be simultaneous or sequential.

For administration, the antagonists of αvβ5 integrin and second therapeutic agent can be administered at a rate determined by the combined $LD_{50}$ of the antagonist and the second therapeutic agent, and the side-effects of the antagonist and the second therapeutic agent at various concentrations, as applied to the mass and overall health of the subject. In some cases, the antagonists of αvβ5 integrin and second therapeutic agent are each administered at a subtherapeutic dose or a therapeutic dose.

VII. Kits

The present invention also provides kits for treating or preventing diseases involving αvβ5 integrin, including, e.g., PE, stroke, myocardial infarction, and cancer (i.e., angiogenesis). The kits comprise an antagonist of αvβ5 integrin (e.g., an antibody that binds to αvβ5 integrin, including e.g., ALULA, humanized ALULA, or fragments of ALULA), and antibody that binds to β5 (e.g., ALULA, humanized ALULA, or fragments of ALULA), and antibody that competes with ALULA) and a second therapeutic agent for treatment of a disease involving αvβ5 integrin, including PE. Suitable second therapeutic agents include, e.g., a TGFβ pathway inhibitor, activated Protein C, a steroid, GM-CSF, a platelet inhibitor, a diuretic agent; a bronchodilating agent, antibodies that specifically bind to αvβ5 integrin or β5, a second antagonist of αvβ5 integrin, antibodies that specifically bind to a αvβ6 integrin, antagonists of αvβ6 integrin, β-2 agonists, and surfactants. The kits may also comprise written instructions (e.g., a manual) for using the kit.

EXAMPLES

Example 1

Materials and Methods

Rodent Single Lung Ischemia-Reperfusion Lung Injury Model of PE: Mice or rats undergo lung transplantation, cardiopulmonary bypass, pulmonary thromboendoarterectomy, or severe shock. Next ischemia and reperfusion are induced for thirty minutes and three hours, respectively. To induce ischemia, a left thoracotomy is performed by blocking the left hilum (e.g., with umbilical tape) for 30 minutes. To induce reperfusion, the lungs are reinflated with a tidal volume of 12 ml/kg of air and then normal ventilation is resumed. The animals are euthanized after 3 hours and the permeability of each lung is assessed, e.g., by measuring labeled albumin extravasation into the lung, expressed as extravascular pulmonary equivalents (EVPE).

Rodent Ventilator-Induced Lung Injury Model of PE: Mice or rats are ventilated with normal (6 ml per kg) or high tidal volume (20 ml per kg). Animals are injected with $^{125}$I-labeled albumins after 4 hours and then lungs are harvested and EVPE determined.

Measurement of Extravascular Plasma Equivalents (EVPE): EVPE were measured as described in, e.g., Frank et al., *J. Biol. Chem.*, 278 (45): 43939-43950 (2003)). Briefly, a vascular tracer (e.g., $^{125}$I albumin) is injected intraperitoneally into rats two hours before lung harvest. Blood is collected and the lungs are removed. Lung and plasma radioactivity are measured. Hemoglobin concentration is measured in the lung homogenate and in the blood. Lung intravascular radioactivity is calculated multiplying the plasma radioactivity count by the blood volume in the lung.

Antibodies: ALULA was generated as described below. W6/32, a murine monoclonal antibody W6/32 which specifically binds to HLA A, B, and C was obtained from ATCC. CD-1 WT, a monoclonal antibody that binds to CD-1 was obtained from ATCC.

Example 2

Generation of ALULA, a Murine Monoclonal Antibody that Specifically Binds to αvβ5 Integrin αvβ5 knockout mice were immunized with cells expressing a polypeptide comprising an αvβ5 integrin sequence. Monoclonal antibodies that specifically bind αvβ5 integrin were identified using methods known in the art. More particularly, ALULA which specifically binds to β5 was identified. ALULA was deposited with the ATCC on Feb. 13, 2004 and has the following Accession No.: PTA-5817.

Example 3

β5$^{-/-}$ Mice Do not Develop Lung Injury Associated PE

β5$^{-/-}$ mice and wild type mice were ventilated as described in Example 1 above to induce PE associated with lung injury and EVPE was determined. In contrast to the wild-type mice, β5$^{-/-}$ mice did not develop PE after ventilation. These results indicate that αvβ5 is involved in PE. The results are shown in FIG. 1.

Example 4

A Monoclonal Antibody that Specifically Binds to β5 Reduces the Severity of Pulmonary Edema Associated with Ischemia Reperfusion To determine the role of β5 in PE associated with ischemia-reperfusion, rats were given the following treatments and EVPE measurements were taken:
1. No treatment.
2. Intraperitoneal (i.p.) injection 4 μg per gram of W6/32.
3. I.p. 4 μg per gram (i.p.) of ALULA.
4. Ischemia-reperfusion was induced as described in Example 1 above
5. Ischemia-reperfusion was induced and 4 μg per gram of W6/32 was injected intraperitoneally.
6. Ischemia-reperfusion was induced and 4 μg per gram of ALULA was injected intraperitoneally.

In these experiments, antibodies were injection prior to induction of ischemia-reperfusion.

Rats that received treatment with ALULA exhibited reduced EVPE (i.e., reduced lung cell permeability) compared to control rats, indicating that a monoclonal antibody that specifically binds to β5 can reduce the severity of PE.

Figure 2:
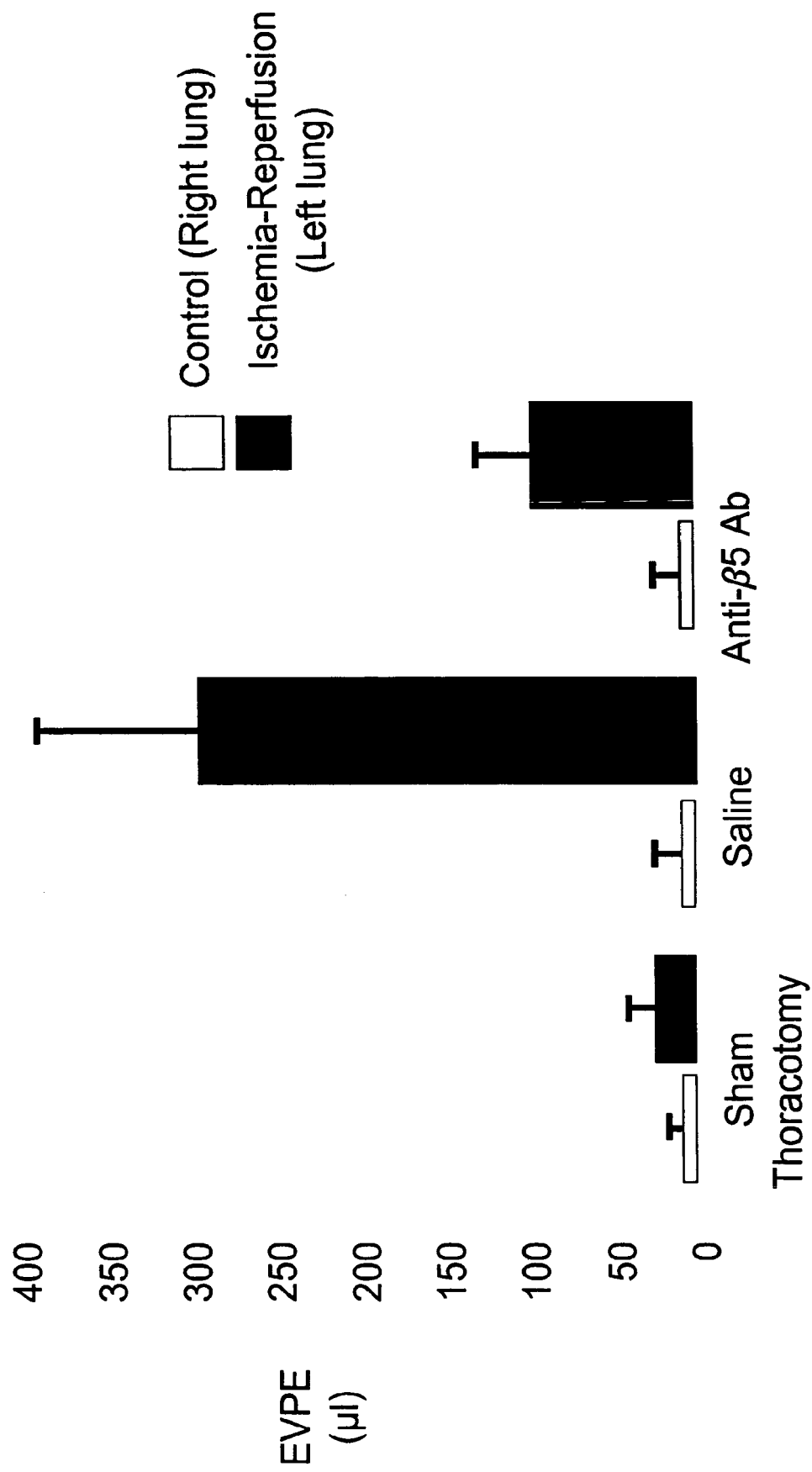
FIG. 2 illustrates results from in vivo experiments that demonstrate that an antibody that specifically binds to β5 (i.e., ALULA) reduces the severity of ischemia reperfusion induced PE.

The results are shown in FIG. 2.

Example 5

A Monoclonal Antibody that Specifically Binds to β5 Reduces the Severity of Pulmonary Edema Associated with Lung Injury To determine the role of β5 in PE associated with lung injury, mice were given the following treatments and EVPE measurements were taken:
1. Normal tidal volume and i.p. injection of 4 μg per gram of CD-1 WT.
2. High tidal volume and i.p. injection of 4 μg per gram of CD-1 WT.
3. Normal tidal volume and i.p. injection of 4 μg per gram of ALULA.
4. High tidal volume and i.p. injection of 4 μg per gram of ALULA.

In these experiments, antibodies were injection prior to tidal volume treatments.

Mice that received treatment with ALULA exhibited reduced EVPE compared to control mice, indicating that a monoclonal antibody that specifically binds to β5 can reduce the severity of PE.

Thus, ALULA is the first monoclonal antibody specific for αvβ5 that has been shown to have blocking activity in vivo in whole mammals and is the first shown to block increased vascular permeability and the development of alveolar flooding in models of acute lung injury (i.e., PE).

Figure 3:
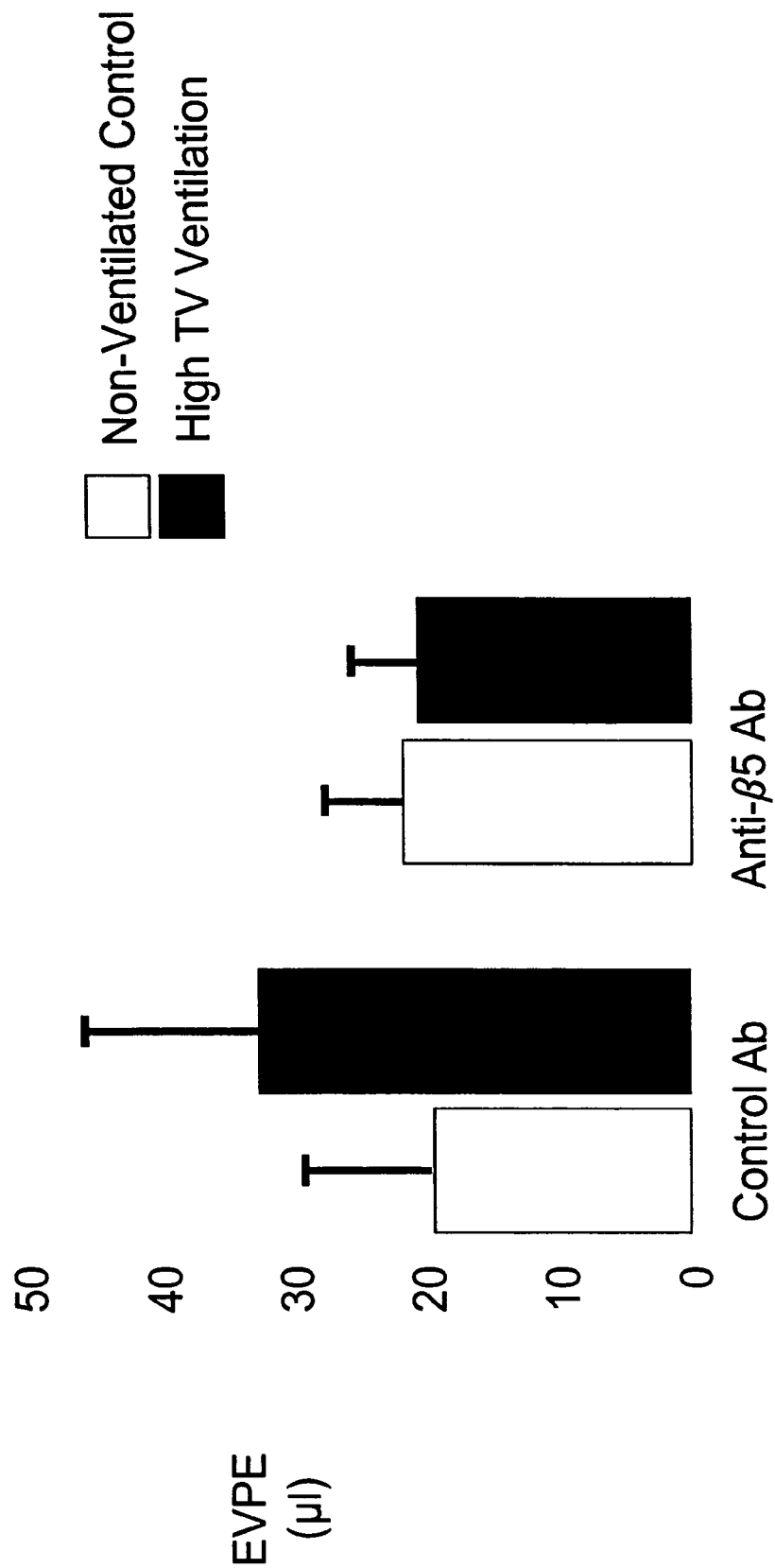
FIG. 3 illustrates results from in vivo experiments that demonstrate that an antibody that specifically binds to β5 (i.e., ALULA) reduces the severity of induced by lung injury from large tidal volume ventilation.

The results are shown in FIG. 3.

Example 6

Figure 4:
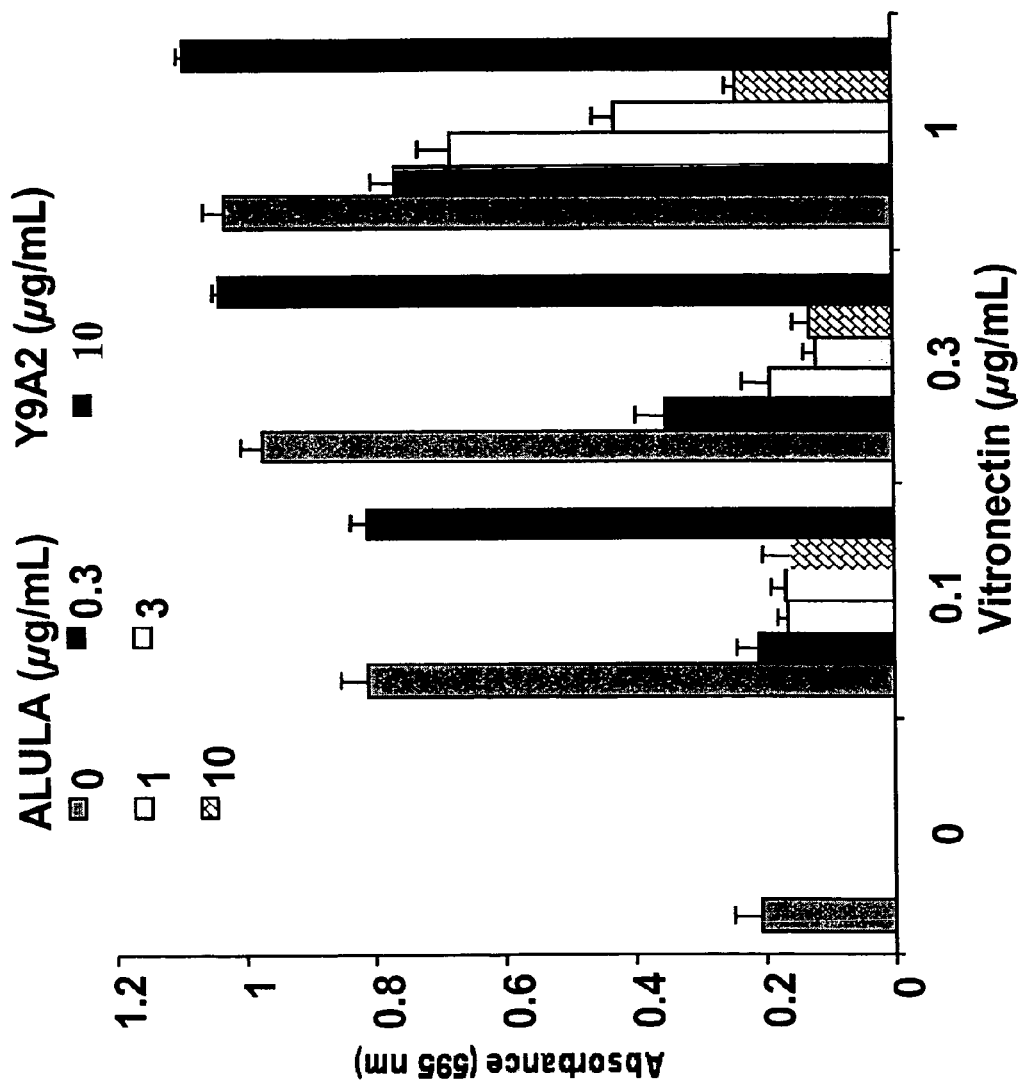
FIG. 4 illustrates results from in vitro experiments that demonstrate that an antibody that specifically binds to β5 (i.e., ALULA) blocks adhesion of cells expressing αvβ5 integrin to dishes coated with a range of concentrations of the αvβ5 integrin ligand, vitronectin.

Antibody ALULA Blocks Binding of the αvβ5 Integrin Ligand Vitronectin to Cells Expressing αvβ5 Integrin SW-480 cells expressing αvβ5 integrin are contacted with 0 μg/ml, 0.1 μg/ml, 0.3 μg/ml, and 1 μg/ml of vitronectin in the presence of 0 μg/ml, 0.3 μg/ml, 1 μg/ml, and 10 μg/ml of ALULA. A monoclonal antibody (i.e., Y9A2) specific for α9β1 integrin is used as a negative control. ALULA blocks binding of the αvβ5 integrin ligand, vitronectin, to the cells. The results are shown in FIG. 4.

The above examples are provided to illustrate the invention but not to limit its scope. Other variants of the invention will be readily apparent to one of ordinary skill in the art and are encompassed by the appended claims. All publications, databases, patents, patent applications, and accession nos. cited herein are hereby incorporated by reference in their entirety for all purposes.

What is claimed is:

1. An isolated antibody that binds the same epitope of αvβ5 as bound by ALULA (the antibody produced by the hybridoma as deposited under ATCC Deposit No. PTA-5817).

2. The antibody of claim 1, wherein the antibody is ALULA (the antibody produced by the hybridoma as deposited under ATCC Deposit No. PTA-5817).

3. The antibody of claim 1, wherein the antibody is a humanized ALULA.

4. The antibody of claim 1, wherein the antibody is selected from the group consisting of: a scFv, a Fab, and a (Fab')2.

5. A pharmaceutical composition comprising a pharmaceutically acceptable excipient and the antibody of claim 1.

6. The pharmaceutical composition of claim 5, wherein the antibody is ALULA the antibody produced by the hybridoma as deposited under ATCC Deposit No. PTA-5817).

7. The pharmaceutical composition of claim 5, wherein the antibody is a humanized ALULA.

8. The pharmaceutical composition of claim 5, further comprising a second therapeutic agent for treating acute lung injury.

9. A method of treating pulmonary edema in a mammalian subject, the method comprising administering a therapeutic amount of the pharmaceutical composition of claim 5 to the subject.

* * * * *